US006611828B1

(12) United States Patent
Koleszar et al.

(10) Patent No.: US 6,611,828 B1
(45) Date of Patent: Aug. 26, 2003

(54) GRAPHICAL VIEWER FOR BIOMOLECULAR SEQUENCE DATA

(75) Inventors: Alex George Koleszar, Newark, CA (US); Jeanette Schmidt, Palo Alto, CA (US); Megan E. Grether, San Francisco, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 293 days.

(21) Appl. No.: 09/776,651

(22) Filed: Feb. 2, 2001

Related U.S. Application Data

(63) Continuation-in-part of application No. 09/362,649, filed on Jul. 27, 1999, now Pat. No. 6,519,583, which is a continuation-in-part of application No. 08/856,647, filed on May 15, 1997, now Pat. No. 5,970,500, and a continuation-in-part of application No. 08/857,382, filed on May 15, 1997, now Pat. No. 5,966,712.
(60) Provisional application No. 60/256,863, filed on Dec. 19, 2000.

(51) Int. Cl.[7] .............................................. G06F 17/30
(52) U.S. Cl. .................. 707/1; 345/765; 435/6
(58) Field of Search .................. 707/1, 6, 10, 104.1, 707/3; 345/764, 765; 935/6

(56) References Cited

U.S. PATENT DOCUMENTS

| 5,418,944 | A | 5/1995 | DiPace et al. ................ 707/3 |
| 5,523,208 | A | 6/1996 | Kohler et al. ................ 435/6 |
| 5,706,498 | A | 1/1998 | Fujimiya et al. ............... 707/6 |
| 5,840,484 | A | 11/1998 | Seilhamer et al. .............. 435/6 |
| 5,953,727 | A | 9/1999 | Maslyn et al. .............. 707/104.1 |
| 5,966,712 | A | 10/1999 | Sabatini et al. ............ 707/104.1 |
| 5,970,500 | A | 10/1999 | Sabatini et al. ............ 707/104.1 |
| 6,023,659 | A | 2/2000 | Seilhamer et al. .............. 702/19 |
| 6,189,013 | B1 | 2/2001 | Maslyn et al. ............. 707/104.1 |
| 6,363,399 | B1 | 3/2002 | Maslyn et al. .............. 707/104 |

FOREIGN PATENT DOCUMENTS

WO   WO 96/23078   8/1996

OTHER PUBLICATIONS

Larsen, et al., "The ribosomal database project", 1993, Nucl. Acids Res., vol. 21, No. 13, pp. 3021–3023.
Duret, et al., "HOVERGEN: a database of homologous vertebrate genes", 1994, NAR, vol. 22, No. 12, pp. 2360–2365.
Adams, "Complementary DNA Sequencing: Expressed Sequence Tags and Human Genome Project", Jun. '91, Science vol. 252, pp. 1651–1656.
Matsubara, et al., "Identification of new genes by systematic analysis of cDNAs and database construction", 1993 Biotech. 4, pp. 671–677.
Kanehisa, "Toward Pathway Engineering: A New Database of Genetic and Molecular Pathways", 1996, Science & Tech Japan, No. 59, pp. 34–38.
Gaasterland, et al., "Using Multiple Tools for Automated Genome Interpretation in an Integrated Environment", 1996, 6 pages.

(List continued on next page.)

Primary Examiner—Jack M Choules
(74) Attorney, Agent, or Firm—Beyer, Weaver & Thomas, LLP

(57) ABSTRACT

Disclosed are methods, media and systems for graphically displaying computer-based biomolecular sequence information. Generally, biomolecular sequence information may be graphically depicted in a variety of different forms in accordance with the present invention. The sequence information may be composed of nucleotide or amino acid sequence information or both. The graphical depictions may be in several different formats providing different information relating to the sequences, and may be displayed in one or more screens of a computer user interface.

63 Claims, 15 Drawing Sheets

OTHER PUBLICATIONS

"The GenBank DNA Sequence Database", NCBI, Mar. 1996, 7 pages.
"GenBank Overview", NCBI, Oct. 1997, 2 pages.
Gaasterland, et al., "MAGPIE—MAGPIE Automated Genome Project Investigation Environment", 4 pages.
"Guide to WWW Entrez Genomes Division", NCBI Entrez, 12 pages.
"Saccharomyces Genome Database", Stanford Genomic Resources, 4 pgs.
TIGR Database, The Inst. For Genomic Research, www.tigr.org © 1997 TIGR.
GSDB—Genome Sequence DataBase, http://wehih.wehi.edu.au/gsdb/ 3 pp.
Green et al., "Ancient conserved regions in new gene sequences and the protein databases", (3/93) © 1997 UMI, Dialog File 484, Item 5, Periodical Abstracts 9 pgs.
Martin, et al., "Accessing genetics databases", (2/94) © 1998 Info Access Co., Dialog File 148: IAC Trade & Ind. Database, Item 2, 10 pgs.
ISSN 0258–851X, "In Vivo the Business & Medicine Report", (5/96) © 1998 Information Access Co., Dialog File 16: IAC PROMT, Item 1, 6 pgs.
Waldrop, "On–line archives let biologists interrogate the genome", (9/95), © 1997 UMI, Dialog File 484: Periodical Abstracts Plus, Item 7, 5 pgs.
LifeSeq—Release 3.4—Jan. 1996, Sequences: 319, 869; Libraries: 105.
LifeSeq—Version 4.0—Apr. 1996, Sequences: 667, 742; Libraries: 163.
LifeSeq—Version 4.1—Jul. 1996; Sequences: 912, 171; Libraries: 207.
LifeSeq—Version 4.2—Oct. 1996; Sequences 1, 255, 791; Libraries: 274.
LIFESEQ™ Training Course (manual), 201 pp., © 1996 Incyte Pharmaceuticals, Inc.
Akerblom, "Introduction to the LIFESEQ Database", 46 pp. (from manual, see #32 above).
Stuart, "cDNA Library Constructing and Cloning", 10 pp.(from manual, see #32 above).
Cathcart, et al., "Overview of Sequencing and Bioinformatics", 7 pp.(from manual, see #32 above).
Delegeane, et al., "Automated Bioanalysis", 36 pp.(from manual, see #32 above).
Akerblom, "Using the LIFESEQ Database", 42 pp.(from manual, see #32 above).
Wilde, "Working with Sequence Data, Part 1", 18 pp.(from manual, see #32 above).
Braxton, "Working with Sequence Data, Part 2", 19 pp.(from manual, see #32 above).

*Genomic Query Results*

Search Criteria: Where Keyword="kinase"
Query Hits: 6

☐ 1) GBI:g1869771   Viewer   FASTA
Human DNA sequence from PAC 296K21 on chromosome X contains cytokeratin exon, delta-aminolevulinate synthase (erythroid), 5-aminolevulinic acid synthase, (EC 2.3.1.37). 6-phosphofructo-2-kinase/fructose-2,6-bisphoshatase (EC2.7.1.105, EC 3.1.3.46), ESTs and STS.

☐ 2) GBI:g3150091   Viewer   FASTA
Homo sapiens DNA sequence from PAC 884M20 on chromosomes Xp11.21. Contains cytokeratin exon, delta-aminolevulinate synthase (erythroid), 5-aminolevulinic acid synthase, (EC 2.3.1.37). 6-phosphofructo-2-kinase/fructose-2,6-bisphoshatase (EC2.7.1.105, EC 3.1.3.46), ESTs and STS, complete sequence.

☐ 3) GBI:g3445456   Viewer   FASTA
Human DNA sequence from clone 325F22 on chromosome 6q23.1-24.3. Contains the MEKK5 (ASK1, MAPKKK5) gene for MAP/ERK kinase kinase 5 (Mitogen Activated Protein kinase kinase kinase 5), ESTs, GSSs and a putative CpG island, complete sequence.

☐ 4) GBI:g5263010   Viewer   FASTA
Human DNA sequence from clone RP3-402G11 pm chromosome 22q13.31-13.33.Contains the MAPK12 gene for mitogen activated protein kinase 12 (SAPK3), the MAPK 11 gene for mitogen activated protein kinase 11 (PRKM11), gene KIAA0315, the gene for a novel protein similar to KIAA091 and mouse histone deacetylase MHDA2, the gene for a novel protein similar to Xenopus gamma-tubulin interacting protein (yeast SPC98 homolog), the gene for a novel protein similar to yeast and bacterial predicted proteins, the gene for a novel protein similar to C. elegans F38A5.s, athe gene for a novel protein similar to MRS1 and the gene for a novel protein similar to mouse MOV10 (GB10) and yeast and plant predicted proteins. Contains ESTs, GSSs and fifteen putative CpG islands, Complete sequence.

FIG. 2

GRAPHICAL VIEWER FOR BIOMOLECULAR SEQUENCE DATA

CROSS-REFERENCE TO RELATED APPLICATIONS

This application is a continuation-in-part of application Ser. No. 09/362,649, filed Jul. 27, 1999, now U.S. Pat. No. 6,519,583, entitled GRAPHICAL VIEWER FOR BIOMOLECULAR SEQUENCE DATA, which is a continuation-in-part of application Ser. No. 08/856,647, filed May 15, 1997, now U.S. Pat. No. 5,970,500, entitled DATABASE AND SYSTEM FOR DETERMINING, STORING AND DISPLAYING GENE Locus INFORMATION, and application Ser. No. 08/857,382, filed May 15, 1997, now U.S. Pat. No. 5,966,712, entitled DATABASE AND SYSTEM FOR STORING, COMPARING AND DISPLAYING GENOMIC INFORMATION, the disclosures of all of which are incorporated by reference herein for all purposes. Moreover, this application also claims priority to provisional patent application Ser. No. 60/256,863, filed Dec. 19, 2000, entitled GRAPHICAL VIEWER FOR BIOMOLECULAR SEQUENCE DATA which is hereby incorporated by reference herein for all purposes.

BACKGROUND OF THE INVENTION

The present invention relates generally to the field of bioinformatics. In particular, the invention relates to methods, media and systems for graphically displaying computer-based biomolecular sequence information.

Informatics is the study and application of computer and statistical techniques to the management of information. Bioinformatics includes the development of methods to search computer databases of biomolecular sequence information (e.g., nucleic acid and protein) quickly, to analyze and display biomolecular sequence information, and to predict protein sequence, structure and function from DNA sequence data.

Increasingly, molecular biology is shifting from the laboratory bench to the computer desktop. Today's researchers require advanced quantitative analyses, database comparisons, and computational algorithms to explore the relationships between sequence and phenotype. Thus, by all accounts, researchers cannot and will not be able to avoid using computer resources to explore gene sequencing, gene expression, and molecular structure.

One use of bioinformatics involves studying an organism's genome to determine the sequence and placement of its genes and their relationship to other sequences and genes within the genome or to genes in other organisms. Such information is of significant interest in biomedical and pharmaceutical research, for instance to assist in the evaluation of drug efficacy and resistance. To make genomic information manipulation easy to perform and understand, sophisticated computer database systems have been developed. Incyte Genomics, Inc. of Palo Alto, Calif., has developed several such databases (for example LifeSeq® Gold), including some in which genomic sequence data is electronically recorded and annotated with information available from public sequence databases. Examples of such public sequence databases include GenBank (NCBI) and SWIS-SPROT. The resulting information is stored in a relational database that may be employed to determine relationships between sequences and genes within and among genomes.

While genetic data processing and relational database systems such as those developed by Incyte Genomics, Inc. provide great power and flexibility in analyzing genetic information, further improvements in these systems will help accelerate biological research for numerous applications.

One area of interest in this regard is the display and viewing of biomolecular sequence information. As noted above, an important goal of genome research to determine the sequence and placement of an organism's genes and their relationship to other sequences and genes within the genome, to genes in other organisms, and to related protein sequences. The ability to clearly and effectively display gene loci information for a given organism or organisms would greatly assist this task.

Accordingly, the development of a display viewing tool which allows a user to clearly and effectively display gene loci information for a given organism or organisms and/or other biomolecular sequence information is desirable.

SUMMARY OF THE INVENTION

The present invention meets this and other needs by providing methods, media and systems for graphically depicting computer-based biomolecular sequence information. Generally, biomolecular sequence information may be graphically depicted in a variety of different forms in accordance with the present invention. In particular, the tools of the present invention facilitate data manipulation permitting detailed analysis of selected portions of the biomolecular sequence information. The biomolecular sequence information may be composed of nucleotide or amino acid sequence information or both. The graphical depictions may be in several different formats providing different information relating to the sequences, and may be displayed in one or more screens of a computer user interface.

A graphical viewer in accordance with the present invention preferably has a plurality of panels, each panel displaying information about the biomolecular sequence data of interest in a different way. For example, a first panel could show a graphical representation of an entire biomolecular sequence, or a portion of the sequence of interest, with the locations of particular sub-sequences of interest indicated. A second panel could show a more detailed graphical representation of all or a selected portion of the sequence represented in the first panel, allowing a user to focus on particular sub-sequences of interest. This second panel view could depict additional information, relating to the particular subsequences of interest. A third panel could show additional information which may include annotations or graphical representations of the number or type of sequencing operations used to generate the biomolecular sequence data. Alternatively, the third panel could show confidence level, or origination, for example, of the biomolecular sequence data represented in one or more of the other panels. Additional panels on the same or additional screens could show, for example, the actual nucleotide or amino acid sequence of, or relating to, a selected subsequence of interest represented in one or more of the other panels, or other information relating to the biomolecular sequence data. Also, additional panels may comprise one or more Working Basket panels which could show, for example, nucleotide or amino acid sequence information selected from among the other panels and collected in the Working Basket panel wherein further detailed analysis could be conducted on the collected sequence information.

In accordance with the present invention, one embodiment comprises a computer implemented method for presenting biomolecular sequence data. This embodiment includes retrieving biomolecular sequence data from a database and graphically depicting elements of the biomolecular sequence data in a user interface of a computer system. The data can be retrieved in response to a user generated query. Additionally, one or more components of the depicted biomolecular sequence data are graphically selected. A further embodiment can comprise displaying the biomolecular sequence data in a plurality of panels comprised within a single frame. Still another embodiment of the present invention can include graphically selecting the one or more components of the biomolecular sequence data by selecting the components of the biomolecular sequence data as a group of biomolecular sequence data or individually selecting the components of biomolecular sequence data. In one embodiment, the selected data can be stored in a Working Basket panel.

One preferred embodiment includes a method for retrieving the biomolecular sequence data, presenting biomolecular sequence data in the plurality of panels which include a first legend panel graphically depicting at least a portion of a biomolecular sequence associated with a reference ID, a second target or reference panel graphically depicting at least a portion of the biomolecular sequence depicted in said legend panel, and a third panel which can selectably indicate further information including annotated information or details concerning the number and type of sequencing operations conducted to determine the sequence data depicted in other panels.

Another aspect of the invention is reflected in an embodiment wherein the graphically selected components of biomolecular sequence data stored or displayed in a Working Basket panel are subjected to further detailed analysis. Additional methods of further analyzing the sequences include manipulating the data in the third panel to conduct the detailed analysis by scrolling up and down the third panel to further examine details of the biomolecular sequence data displayed therein. In one particular embodiment the details examined can include the number and type of sequencing operations used to determine the biomolecular sequence data. Another aspect embodied by the invention includes highlighting graphically selected components of biomolecular sequence data, wherein the highlighted data can be hidden from view on selected panels leaving viewable certain remaining biomolecular sequence data. In addition to making easily viewable the desired information, this aspect of the embodiment, allows the viewable remaining biomolecular sequence data to be manipulated to analyze the viewable data in detail, wherein such manipulation can be accomplished by scrolling up and down panels displaying the viewable data.

An additional method of embodiment of the invention comprises a computer implemented method having programming instructions allowing a user to focus in on certain biomolecular sequence data of interest by retrieving biomolecular sequence data from a database, graphically depicting the data in a plurality of panels displayed on a user interface of a computer system, and graphically selecting one or more components of the biomolecular sequence data. Also, the programming instructions can include a user generated query which determines which biomolecular sequence data is to be retrieved. The programming instructions enable the graphically selected components of the biomolecular sequence data to be stored and analyzed in a Working Basket. Alternatively, or additionally, the embodiment includes programming instructions for highlighting the graphically selected one or more components of the biomolecular sequence data, and for hiding from view the highlighted data leaving viewable certain remaining biomolecular sequence data. The programming instructions can also include instructions enabling the viewable remaining biomolecular sequence data to be manipulated to analyze the viewable data in detail, wherein such manipulation can be accomplished by scrolling up and down panels displaying the viewable data.

In still another aspect, the invention provides a computer-readable medium containing programmed instructions arranged to graphically depict biomolecular sequence data. The computer-readable medium includes programmed instructions for retrieving biomolecular sequence data from a computer system database in response to a user query, and graphically depicting elements of the biomolecular sequence data in a user interface for the computer system. Additionally the embodiment includes instructions enabling graphically selecting one or more components of the biomolecular sequence data. These graphically selected components of biomolecular sequence data can be graphically displayed in a manner which depicts the further detailed sequence information which can include, but is not limited to, the number and type of sequencing operations used to generate the biomolecular sequence data. Further embodiments of the invention can store the graphically selected components of biomolecular sequence data in a Working Basket, wherein the contents of the Working Basket can be manipulated to provide further analysis of the biomolecular sequence data.

In yet another embodiment a computer system comprises a database including biomolecular sequence data configured in a format having a plurality of data fields independent of the source of the data and a user interface capable of receiving from the database, biomolecular sequence data responsive to a query and graphically displaying the biomolecular sequence data in a plurality of panels. Additionally, the database is configured to include data fields comprising a query object handler, a hit object handler, a feature handler, and an analysis tool or method object handler and a unique features object handler. Alternatively, the database is configured to include an object handler which can reformat the biomolecular sequence data into a plurality of data fields which comprise a query object handler, a hit object handler, a feature field, and an analysis tool or method object handler and a unique features object handler.

These and other features and advantages of the present invention will be presented in more detail in the following specification of the invention and the accompanying figures which illustrate by way of example the principles of the invention.

BRIEF DESCRIPTION OF THE DRAWINGS

FIG. 2 is a screen shot (HTML page) depicting a Query Results page for a graphical user interface of a biomolecular sequence database suitable for selecting query hits to be viewed with a biomolecular sequence graphical viewer in accordance with one embodiment of the present invention.

DETAILED DESCRIPTION OF PREFERRED EMBODIMENTS

Figure 1A:
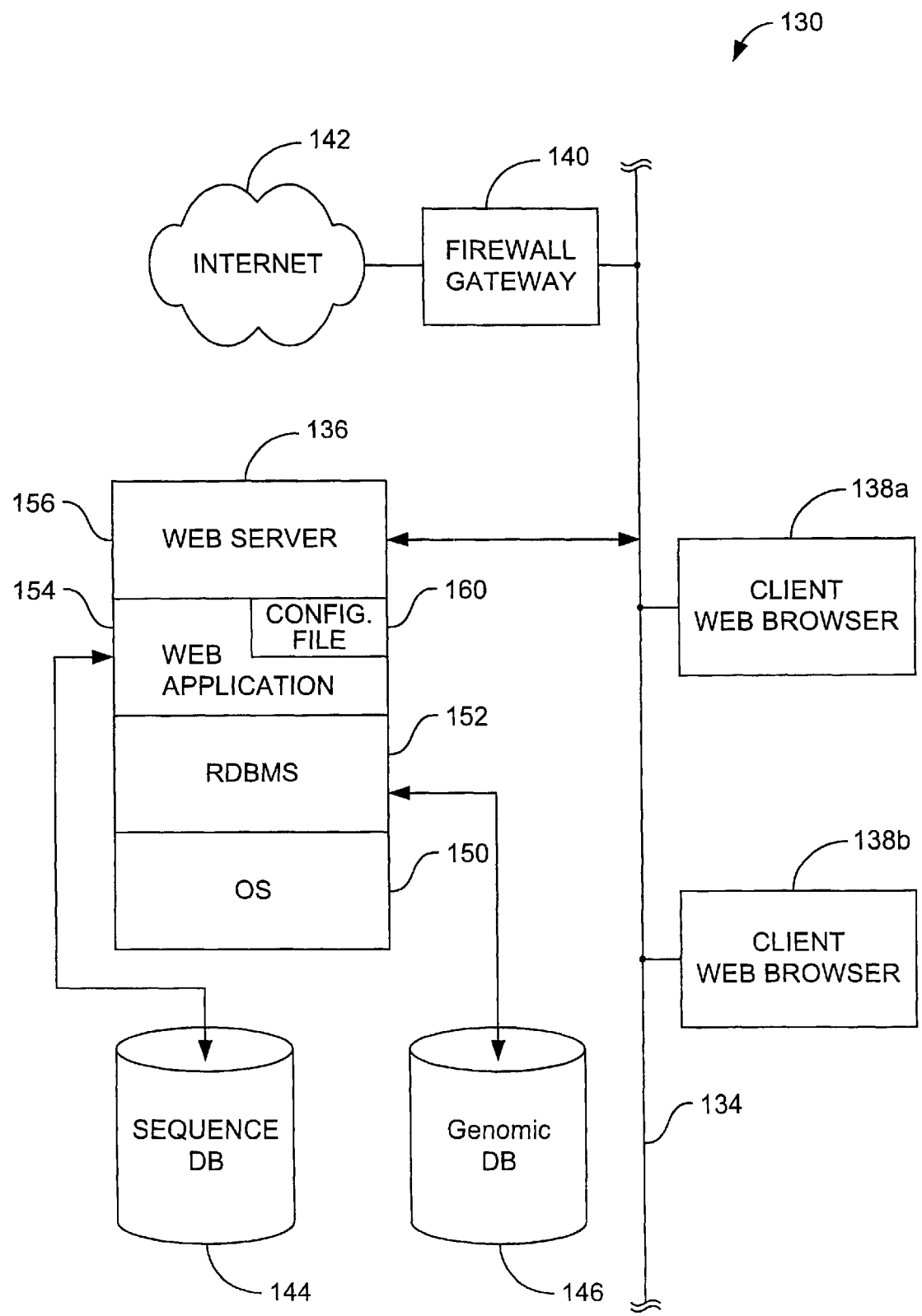
FIG. 1A is a block diagram of a client-server Intranet for providing database services in accordance with one embodiment of the present invention.

Reference will now be made in detail to preferred embodiments of the invention. Examples of the preferred embodiments are illustrated in the accompanying drawings. While the invention will be described in conjunction with these preferred embodiments, it will be understood that it is not intended to limit the invention to one or more preferred embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Introduction

The present invention provides methods, media and systems for graphically displaying computer-based biomolecular sequence information. Generally, biomolecular sequence information may be graphically depicted in a variety of different forms in accordance with the present invention. The sequence information may be composed of nucleotide or amino acid sequence information or both. The graphical depictions may be in several different formats providing different information relating to the sequences, and may be displayed in one or more screens of a computer user interface.

A graphical viewer in accordance with the present invention preferably has a plurality of panels, each panel displaying information about the biomolecular sequence data of interest in a different way on a single screen or page (frame). For example, a first window can include a first legend panel which shows a graphical representation of an entire biomolecular sequence, or the portion of the sequence of interest, with the locations of particular subsequences of interest indicated. Also, the first legend panel can indicate "coverage" over a sequence or sub-sequence. Such "coverage" indicates that a method has been used to determine sequence information for the effected sequence or sub-sequence. A second window comprising a "target" or reference panel could show a more detailed graphical representation of the "coverage" over all or a selected portion of the sequence represented in the first window, allowing a user to focus on a particular sub-sequence of interest. This second window could depict additional information, such as annotations, relating to the particular subsequences of interest. A third panel could, for example, show information such as annotations or graphically represent the number and type of sequencing operations used to obtain the sequence data represented in one or more of the other panels. Also, the third panel can show the confidence level or origination, for example, of the biomolecular sequence data represented in one or more of the other panels. The third panel can also show the method (or analysis tool) used to analyze selected sequence information. The third panel may also be used to depict other sequence information. Additional panels on the same or additional screens could show, for example, the actual nucleotide or amino acid sequence of or relating to a selected sub-sequence of interest represented in one or more of the other panels, or other information relating to the biomolecular sequence data.

In one preferred embodiment, a graphical viewer in accordance with the present invention provides a graphical representation of all or a selected portion of a biomolecular sequence. The viewer allows the user to focus on a particular region or locus of interest and have it also be graphically represented with additional information, such as annotations. A graphical depiction of sequence coverage for the sequence regions represented in the viewer may also be provided.

A graphical viewer in accordance with a preferred embodiment of the present invention preferably provides graphical representations of the biomolecular sequence data in a plurality of panels, each panel displaying information about the biomolecular sequence data of interest in a different way. In a particularly preferred embodiment of the invention, the graphical viewer has three main panels on a single screen: a legend panel or viewer, which always shows the entire portion of the biomolecular sequence under consideration; a target panel or viewer, which allows a user to focus ("zoom in") on areas of the biomolecular sequence portion of particular interest; and, a third panel or viewer. The third viewer can be, for example, a sequence depth viewer, which contains graphical information illustrating the depth of coverage over a length of biomolecular sequence under consideration.

Additionally, a preferred graphical viewer in accordance with the present invention permits the selection of specific biomolecular sequences for addition to a Working Basket panel. The biomolecular sequences stored in the Working Basket can be subjected to further detailed analysis using a variety of analysis tools.

Of course, as noted above, a graphical viewer in accordance with the present invention may be used to display peptide or nucleotide sequence information, and can be used to display actual sequences resulting from comparisons of sequences from, for example, a BLAST or FASTA search.

The Graphical Viewer Environment

Figure 1B:
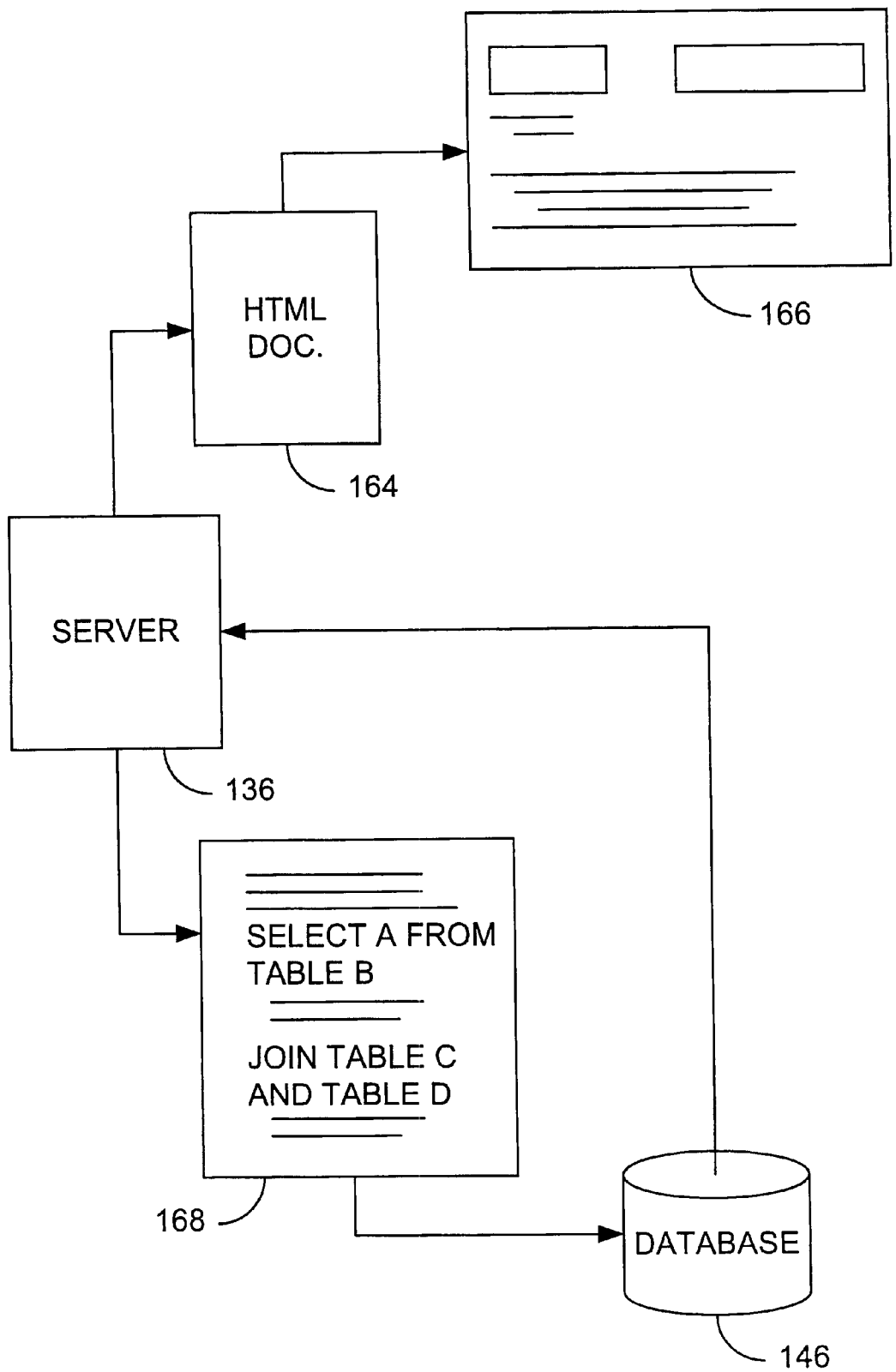
FIG. 1B is a schematic representation of the various software documents and entities employed by the FIG. 1A client-server Intranet to provide biological information in response to user queries.

As noted above, a graphical viewer in accordance with the present invention is preferably used in connection with a biomolecular sequence relational database system, such as those developed by Incyte Genomics, Inc. of Palo Alto, Calif., and described, for example, in patent application Nos. 08/947,845, 08/856,647, 08/811,758, 08/812,290 and 08/857,382, the disclosures of which are incorporated by reference herein for all purposes. Data to be displayed by a graphical viewer in accordance with the present invention is accessed from such a database system using techniques and commands well known to those of skill in the art. FIGS. 1A and 1B and the associated description provided below provide a context in which a graphical viewer in accordance with the present invention may operate.

FIG. 1A depicts a network system 130 suitable for storing and retrieving information in relational databases, such as those suitable for supporting a graphical viewer in accordance with the present invention. Network 130 includes a network cable 134 to which a network server 136 and clients 138a and 138b (representative of possibly many more clients) are connected. Cable 134 is also connected to a firewall/gateway 140 which is in turn connected to the Internet 142.

Network 130 may be any one of a number of conventional network systems, including a local area network (LAN) or a wide area network (WAN), as is known in the art (e.g., using Ethernet, IBM Token Ring, or the like). The network includes functionality for packaging client calls in a well-known format (e.g., URL) together with any parameter information into a format (of one or more packets) suitable for transmission across a cable or wire 134, for delivery to database server 136.

Server 136 includes the hardware necessary for running software to (1) access database data for processing user requests, and (2) provide an interface for serving information to client machines 138a and 138b. In a preferred embodiment, depicted in FIG. 1A, the software running on the server machine supports the World Wide Web protocol for providing page data between a server and client. In this embodiment, a web server 156 having URL and HTTP functionality communicates with a client via the HTTP protocol.

Client/server environments, database servers, relational databases and networks are well documented in the technical, trade, and patent literature. For a discussion of database servers, relational databases and client/server environments generally, and SQL servers particularly, see, e.g., Nath, A., *The Guide To SQL Server*, 2nd ed., Addison-Wesley Publishing Co., 1995 (which is incorporated herein by reference for all purposes).

As shown, server 136 includes an operating system 150 (e.g., UNIX) on which runs a relational database management system 152, a World Wide Web application 154, and a World Wide Web server 156. The software on server 136 may assume numerous configurations. For example, it may be provided on a single machine or distributed over multiple machines.

World Wide Web application 154 includes the executable code necessary for generation of database language statements (e.g., Standard Query Language (SQL) statements). Generally, the executables will include embedded SQL statements. In addition, application 154 includes a configuration file 160 which contains pointers and addresses to the various software entities that comprise the server as well as the various external and internal databases which must be accessed to service user requests. Configuration file 160 also directs requests for server resources to the appropriate hardware—as may be necessary should the server be distributed over two or more separate computers.

Each of clients 138a and 138b includes a World Wide Web browser for providing a user interface to server 136, and including code necessary to generate HTML pages. Through the Web browser, clients 138a and 138b construct search requests for retrieving data from a sequence database 144 and/or a genomic database 146, for example. Thus, the user will typically point and click to user interface elements such as buttons, pull down menus, scroll bars, etc. conventionally employed in graphical user interfaces. The requests so formulated with the client's Web browser are transmitted to Web application 154 which formats them to produce a query that can be employed to extract the pertinent information from sequence database 144 or genomic database 146.

In the embodiment shown, the Web application accesses data in genomic database 146 by first constructing a query in a database language (e.g., Sybase or Oracle SQL). The database language query is then handed to relational database management system 152 which processes the query to extract the relevant information from database 146. In the case of a request to access sequence database 144, Web application 154 directly communicates the request to that database without employing the services of database management system 152.

The procedure by which user requests are serviced is further illustrated with reference to FIG. 1B. In this embodiment, the World Wide Web server and/or executable Web application components of server 136 provide Hypertext Mark-up Language documents ("HTML pages") 164 to a client machine. At the client machine, the HTML document provides a user interface 166 which is employed by a user to formulate his or her requests for access to database 146. That request is converted by the Web application component of server 136 to a SQL query 168. That query is used by the database management system component of server 136 to access the relevant data in database 146 and provide that data to server 136 in an appropriate format. Server 136 then generates a new HTML document, possibly through the Web application 154, relaying the database information to the client as a view in user interface 166.

While the embodiment shown in FIG. 1A employs a World Wide Web server and World Wide Web browser for a communication between server 136 and clients 138a and 138b, other communications protocols will also be suitable. For example, client calls may be packaged directly as SQL statements, without reliance on Web application 154 for a conversion to SQL. Clients may also query the database directly without using a client browser.

When network 130 employs a World Wide Web server and clients, it must support a TCP/IP protocol. Local networks such as this are sometimes referred to as "Intranets." An advantage of such Intranets is that they allows easy communication with public domain databases residing on the World Wide Web (e.g., the GenBank World Wide Web site). Thus, in a particular preferred embodiment of the present invention, clients 138a and 138b can directly access data (via Hypertext links for example) residing on Internet databases using a HTML interface provided by Web browsers and Web server 156.

Bear in mind that if the contents of the local databases are to remain private, a firewall 140 must preserve in confidence the contents of a sequence database 144 and a genomic database 146.

In a preferred embodiment, sequence database 144 is a flat file database with a single file for genomic sequences from different species. Other possible approaches may include partitioning the sequence data according to different species or whether or not sequences have been found to be unique to the local database (i.e., sequences that did not have any hits in an external database such as GenBank).

Preferably, the information in genomic database 146 is stored in a relational format. Such a relational database supports a set of operations defined by relational algebra. It generally includes tables composed of columns and rows for the data contained in the database. Each table has a primary key, being any column or set of columns the values of which uniquely identify the rows in the table. The tables of a relational database may also include a foreign key, which is a column or set of columns the values of which match the primary key values of another table. A relational database is also generally subject to a set of operations (select, project, product, join and divide) which form the basis of the relational algebra governing relations within the database. As noted above, relational databases are well known and documented (see, e.g., Nath, A., *The Guide To SQL Serve,* referenced above).

In one specific implementation, the data used by a viewer embodiment need only be formatted to include a small series of Java®-class object handlers. The only requirements being, a Query Object handler, a Hit Object handler, a Feature Object handler, a Method Object handler, and a Unique Features handler. Alternatively, any formatting device which can convert data into the previously disclosed format is also satisfactory as a formatting implementation.

A relational database may be implemented in different ways. In Oracle™ databases, for example, the various tables are not physically separated, as there is one instance of work space with different ownership specified for different tables. In Sybase™ databases, in contrast, the tables may be physically segregated into different "databases."

One specific configuration for network 130 for multiple users provides both the genomic and sequence databases on the same machine. If there is a high volume of sequence searching, it may be desirable to have a second processor of similar size and split the application across the two machines to improve response time.

A suitable dual processor server machine may be any of the following workstations: Sun-Ultra-Sparc 2™ (Sun Microsystems, Inc. of Mountain View, Calif.), SGI-Challenge L™ (Silicon Graphics, Inc. of Mountain View, Calif.), and DEC-2100A™ (Digitial Electronics Corporation of Maynard, Mass.). Multiprocessor systems (minimum of 4 processors to start) may include the following: Sun-Ultra Sparc Enterprise 4000™, SGI-Challenge XL™, and DEC-8400™. Preferably, the server machine is configured for network 130 and supports TCP/IP protocol.

Depending upon the workstation employed, the operating system may be, for example, one of the following: Sun-Sun OS 5.5 (Solaris 2 5), SGI-IRIX 5 3 (or later), or DEC-Digital UNIX 3 2D (or later).

Databases used in conjunction with this invention may be downloaded via a 4×4 Gb+FWSCSI-2, Fiber Link Raid Units 2OGb+, or 4 DAT Tape Drive. A CD ROM drive may also be acceptable.

The client machine may be, for example, a Macintosh™ (Apple Computer Inc. of Cupertino, Calif.), a PC, or a Unix workstation. It should also be TCP/IP capable with a Netscape or Internet Explorer Web Browser.

The network may include a 10Base-T, 100Base-T or higher connection, be TCP/IP capable, and provide access to Internet for HTML hyperlinks to external databases.

Figure 1C:
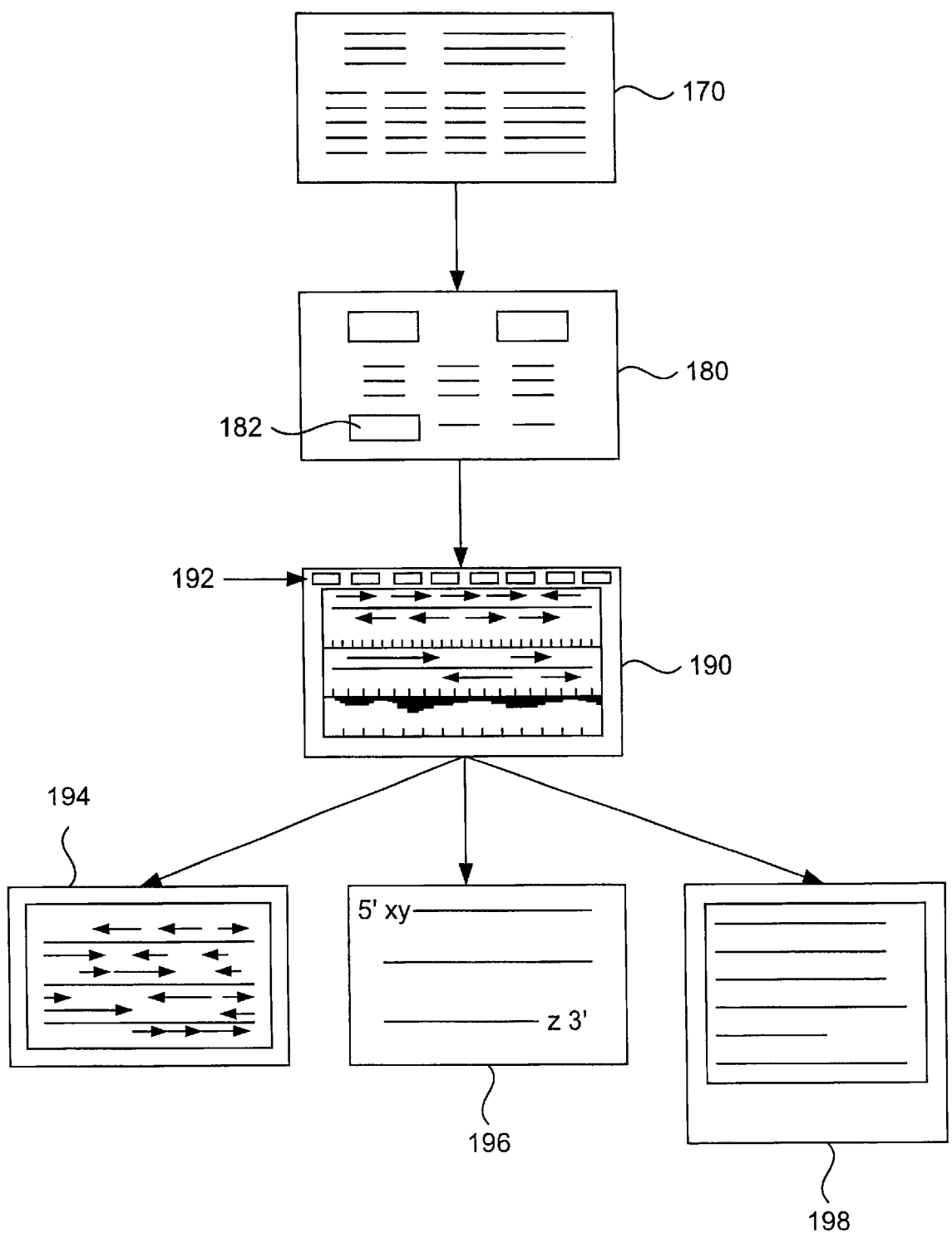
FIG. 1C is a block diagram illustrating the accessibility of graphical viewer features in accordance with a preferred embodiment of the present invention in connection with a biomolecular sequence database.

FIG. 1C illustrates the accessibility of graphical viewer features in accordance with a preferred embodiment of the present invention. A graphical viewer in accordance with the present invention is preferably provided together with a suite of functions made available to users through a collection of user interface screens (e.g., HTML or Java® pages) viewed in the user interface of a biomolecular relational database. Typically, the interface will have a main viewer page from which various lines of query can be followed. In a preferred embodiment, the main viewer page (and other graphical viewers) are Java®-based applets running on the network system. Given the functionalities described herein, one of ordinary skill in the art would be able to implement the graphical viewers of the present invention in Java® or other programming environments. The viewer page is typically accessed from another page provided as part of the user interface of a biomolecular sequence relational database in connection with which the graphical viewer is used.

For example, a user interface screen (e.g., HTML page) 170 displays information relating to a plurality biomolecular sequence databases. One or more sequence databases displayed in the page 170 may be selected, for example, using a pointer or by menu provided in the GUI. Additionally, the type of biomolecular data sought can be specified, e.g., polypeptide or nucleotide. Keywords or specific sequence identifiers can be used to enhance the searches (query). Responsive to the query instructions, another page 180 can display additional information responsive to the query (query hits) about the selected sequences. This page 180 may include numerous details about the query hits and can include a button which when selected accesses a main graphical viewer page 190. The graphical viewer page (e.g., Java® page) 190 graphically depicts information about the selected sequences. The page also preferably includes buttons and menus 192 which allow a user to modify the graphical display. The buttons and menus 192 may also allow access to additional graphical viewer pages 194, 196, which graphically or otherwise display additional information relating to the graphically displayed sequence information in page 190. Additionally, components of the biomolecular sequence data depicted in page 190 can be graphically selected, either in groups or individually. The selected biomolecular sequence data can then be added to a Working Basket which can be viewed as a Working Basket panel 198 containing the selected sequence data.

Viewer Implementation

The invention will now be described with reference to a particular implementation of the invention to graphically depict biomolecular sequence information with reference to a database optimized for human genomic data, such as the LifeSeq® Gold database product developed by Incyte Genomics, Inc. of Palo Alto, Calif., for example. However, application of the present invention is by no means so limited. For example, the invention covers graphical viewers used in connection with databases optimized for other sources of biomolecular sequence data, such as animal sequences (e.g., primate, rodent, amphibian, insect, etc.), microbial sequences (such as that described with reference to grandparent application Ser. No. 08/856,647, previously incorporated by reference), and plant sequences.

As noted above, a graphical viewer in accordance with the present invention is preferably provided together with a suite of functions made available to users through a collection of user interface screens viewed in the user interface of a biomolecular relational database. A main viewer page is typically accessed from another page provided as part of the user interface of a biomolecular sequence relational database in connection with which the graphical viewer is used, in this case a human genomic database. FIG. 2 depicts one such other page from a human genomic database. The Query Results page 180 displays a list of biomolecular sequence information responsive to the query. In the depicted example, a series of "hits" responsive to the query parameters is depicted. For purposes of this application, "hits" shall refer to biomolecular sequence data responsive to the query parameters. For example, a hit may reflect a sequence match between the user specified parameters and other sequences which match the parameters. Also, a hit can reflect a sequence which is a "close" match to the sequence of interest. The hit may comprise an overlap area of identical sequence or a close homology. What comprises a "close" match can depend on a variety of parameters which can be adjusted to determine how near a match is required to qualify as a "close" match. In the example shown in FIG. 2, four query hits 181,182,183,184 are displayed on the depicted page 180 and identified by their LocusIDs 185 (e.g. g1869771) for genes which match a query using the keyword: "kinase" in a human genomic sequence. A total of six query hits are responsive to the query. (See, Query Hits line 187). These additional query "hits" can be accessed by scrolling down the Query Results Page 180 using the scroll bar 188.

Figure 3:
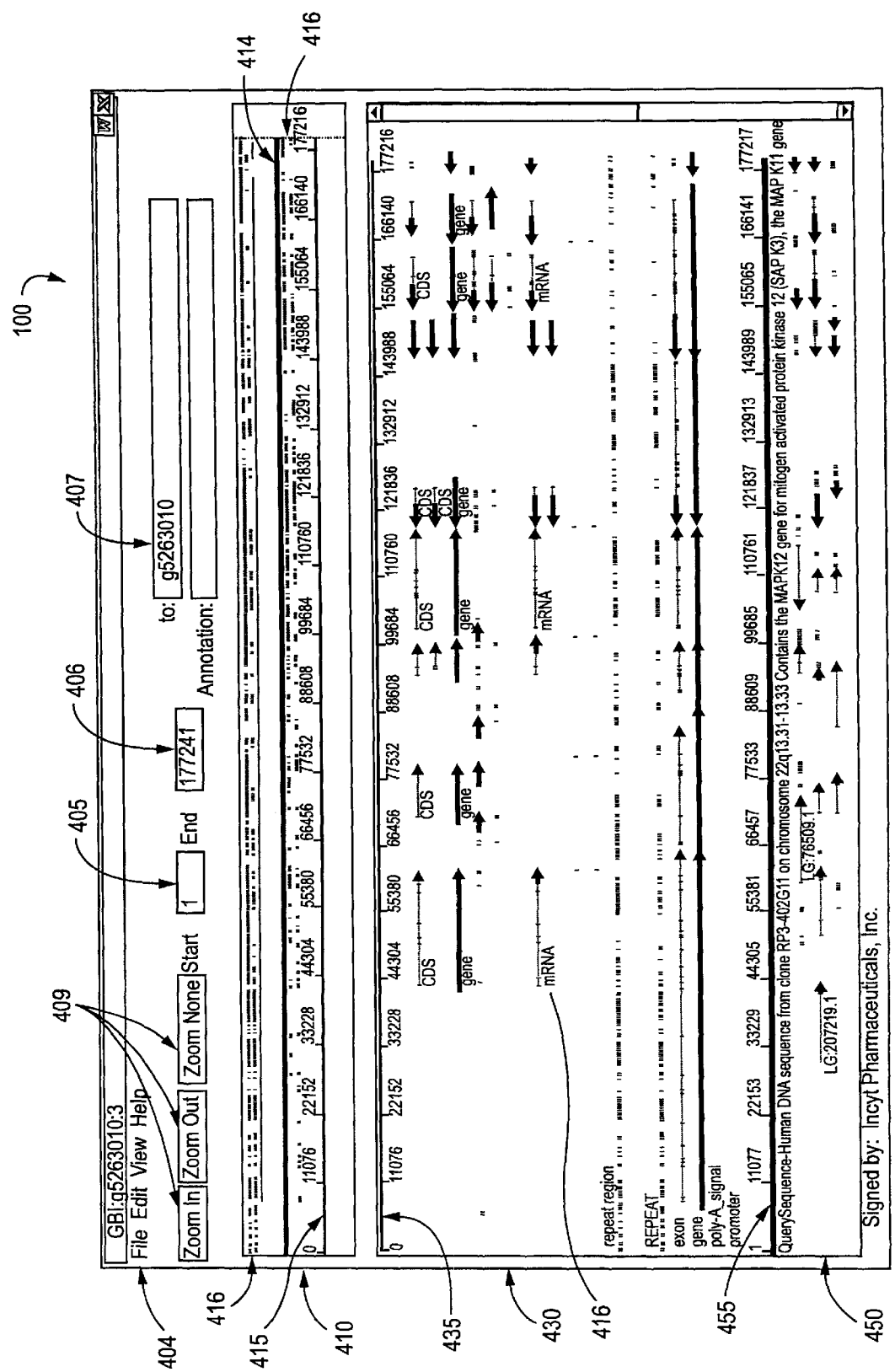
FIG. 3 is a screen shot depicting a page for a graphical user interface, including a legend panel, target panel and third panel, suitable for accessing biomolecular sequence information in accordance with one embodiment of the present invention.

By clicking on the Graphical Viewer button 186 of a particular LocusID (i.e. query "hit") in Query Results Page 180, a user launches a graphical viewer in accordance with the present invention. FIG. 3 depicts a main graphical viewer page 190 accessed by selecting the Graphical Viewer button 186 in Query Results Page 180. In this preferred embodiment, the graphical viewers are Java®-based applets that provide a graphical representation of a portion of a hit and its related loci. A graphical viewer in accordance with the present invention preferably includes a plurality of separate component viewers. Where more than one component viewer is featured it is preferably displayed in a single frame in order to enhance the effectiveness with which the graphically displayed data is conveyed to the user. A preferred embodiment includes three component viewers displayed in a single frame.

Referring to FIG. 3, the graphical viewer page 190, has three viewer component panels 410, 430, 450 on a single screen. The top panel 410 features a "legend viewer" or "legend panel", which shows the entire portion of the sequence under consideration. The middle panel 430 features a second reference target panel, also referred to herein as a "target panel" or "target viewer" 430, which allows a user to focus ("zoom in") on areas of the sequence of particular interest. The bottom or third panel 450 is a selected sub-sequence viewer or panel, which displays information concerning a specific portion of the biomolecular sequence data which can be highlighted or selected using, for example, a mouse or other selection tool. By way of example, one type of information that can be displayed is graphical information illustrating the depth of coverage over, for example, a length of a sequence portion selected from the target viewer 430.

The graphical viewer page 190 also includes several buttons and windows along the top of the page 190 for accessing and displaying additional information. A menu bar 404 is also provided for accessing pull-down menus listing various command and control functions. A scale 415, 435, 455 depicted in each viewer panel 410, 430, 450 offers a reference point which a user may use to provide a location reference concerning the depicted biomolecular sequence data. The use of these features will be described in further detail below.

The legend viewer 410 shows the entire portion of the biomolecular sequence data which was loaded by the viewer in response to user selections in the previous screens. In a preferred embodiment, the viewer will load, for example, a predetermined default number of base pairs of the biomolecular sequence. If the sequence is shorter than the default, the entire sequence will be depicted and the default will be adjusted. For example, in this embodiment, the viewer loads 177,241 base pairs starting at the first locus in the selected item of the Query Results screen 180 (identified by its Hit ID, g5263010). The number of base pairs shown and the position on the sequence may be determined with reference to the scale 415 shown here at the bottom of the legend viewer panel 410. The default value may, of course, be changed to any desired number.

The legend viewer 410 graphically represents, for example, a human DNA sequence from clone RP3-402G11 on chromosome 22q13.31–13.33, as a line 414 which starts at the starting coordinate (base pair number) 1 and extends up to coordinate 177,241, as may be seen with reference to the scale 415. The biomolecular sequence depicted in the viewer can be identified in a ID window 407. In addition, the starting coordinate for the portion of the sequence depicted by the legend viewer 410 (namely, the starting coordinate of the selected locus g5263010: 1) is noted in the Start window 405. And the end coordinate (g5263010: 177,241) is noted in the End window 406. These windows 405, 406, 407 may also be used to enter information in order to control the information depicted by the viewer, as described further below. A user may bring portions of the biomolecular sequence which extend off screen into view in the legend viewer 410 if desired.

In addition to the depicted biomolecular sequence, the legend viewer 410 shows the various loci 416 residing on the depicted portion of the biomolecular sequence. The manner in which these loci are depicted illustrates the power of a graphical viewer in accordance with the present invention in presenting information in a highly effective manner.

The loci can represent "features" of the "hits" returned by the Query Result. The "features" are represented by arrows 416. Each feature 416 is located beside the biomolecular sequence line 414 according to its position on the biomolecular sequence and the direction in which it is read. The arrowhead represents the direction in which a feature 416 is read. Features 416 which are read in the forward (+) direction are depicted above the biomolecular sequence line 414. Features which are read in the reverse (−) direction are depicted below the biomolecular sequence line 414. In addition, other graphical features may be used to convey information about the graphically depicted features. For example, features for which the sequences obtained are above an established confidence threshold may be depicted as broken arrows.

Embodiments can represent the hits and features in different colors based on analysis method or annotation source or other aspects of the hit or feature. For example, a user can select a specific color which will reflect the hits or features associated with a particular method or annotation source. Of course, this tool can accommodate new methods or annotation sources as they are added to the biomolecular sequence data. Of course other categories and colors may also be used. These arrow and color representation tools for features are used in both the legend viewer and the target viewer, discussed below. Additionally, highlighted or selected features can be displayed in different colors, for example, orange. Other highlighting of differentiation schemes can be used to identify highlighted or selected features.

The target viewer 430 initially displays the same scope as the legend viewer 410. The scope of the target viewer 430 may be modified, however, by clicking on the Zoom buttons 409. The Zoom In button provides a closer view of a portion of the biomolecular sequence data shown in the legend viewer 410. The closer view is depicted in the target viewer 430, with the scale 435 adjusting to reflect the amount of the zoom. The Zoom Out button provides a broader view of the biomolecular sequence data, up to the maximum of the default base pair number selected for the legend viewer (minimum magnification). The Zoom None button automatically returns to the minimum magnification.

Figure 4:
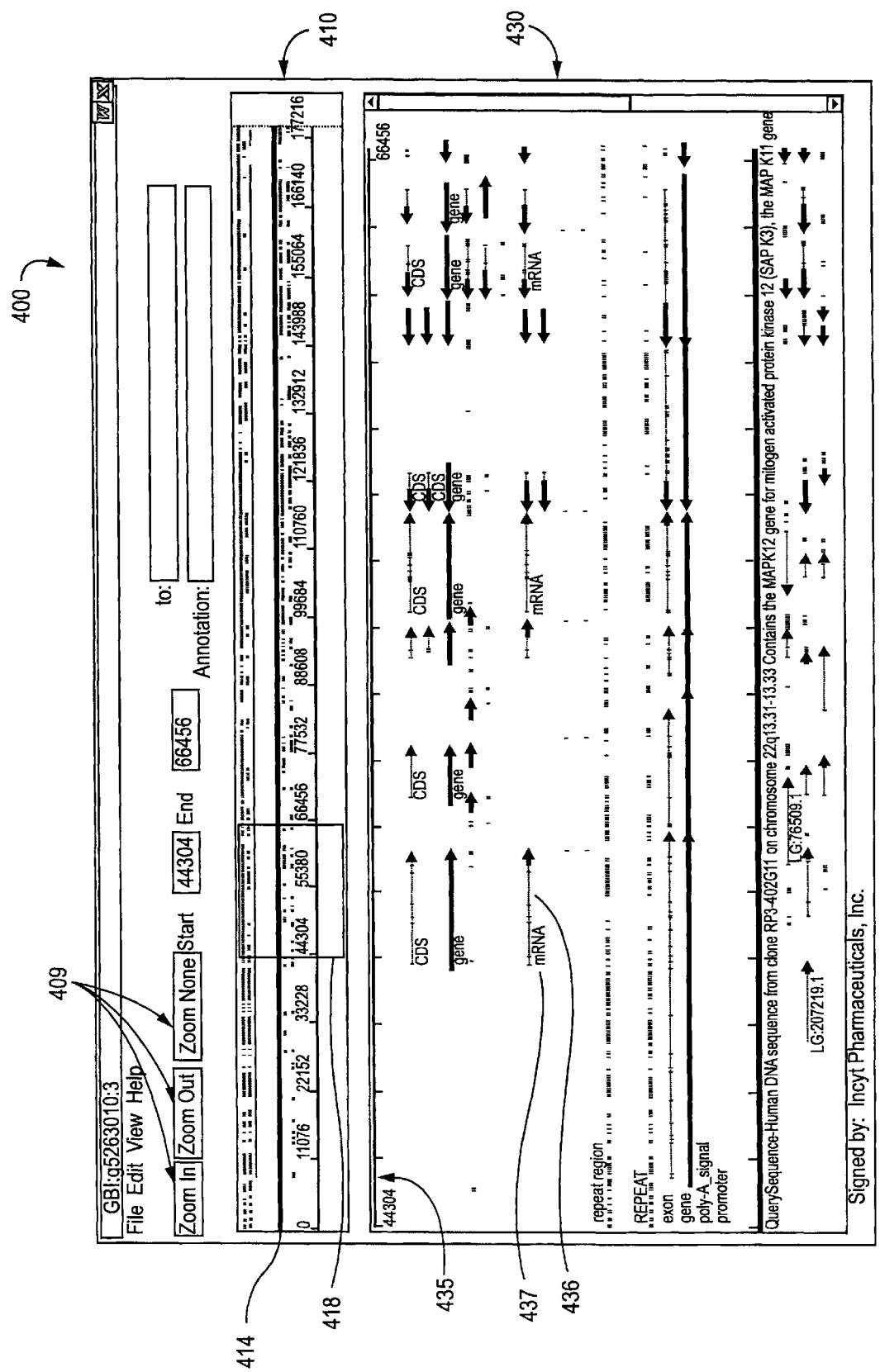
FIG. 4 is a screen shot depicting a main page of a biomolecular sequence graphical viewer with a red "rubber-banded" box in the legend viewer in accordance with one embodiment of the present invention.

Referring to FIG. 4, another way provided by a graphical viewer 400 in accordance with the present invention to focus on a portion of interest of a biomolecular sequence 414 depicted in the legend viewer 410 is to provide an outline 418, such as a colored (e.g., red) box 418, around the portion of the biomolecular sequence 414 which is shown in the legend viewer 410. In this depiction the red box 418 surrounds a selected portion of the legend viewer panel 410, so the target viewer 430 displays base pairs from 44304 to 66456. When the Zoom buttons 409 are used, as described above, the red box 418 is adjusted accordingly.

An area on the biomolecular sequence may also be zoomed into by direct user adjustment of the red box (known as "rubber banding") 418. The scope of the red box 418 may be changed by clicking at a location in any of the viewer panels and dragging the cursor with a mouse to another location. The red box 418 will then encompass the region between those two points, and only this region will be visible in the viewers. FIG. 4 depicts an updated page showing the viewer 400 after a user has zoomed in on the portion of the biomolecular sequence depicted in the legend viewer 410 between about the coordinates 44304 and 66456. The scale 435 of the target viewer 430 has been adjusted to reflect the new scope of the zoomed target view.

Another feature of the target viewer 430 is the features can be annotated. As may be seen in FIG. 4, annotations 437 are provided for feature arrows 436 which are long enough to accommodate the annotation information. If a feature of interest 436 is too short to be display its annotation, a user may zoom in further on the locus until it is long enough to allow the annotation to be displayed in the graphical representation.

Figure 5:
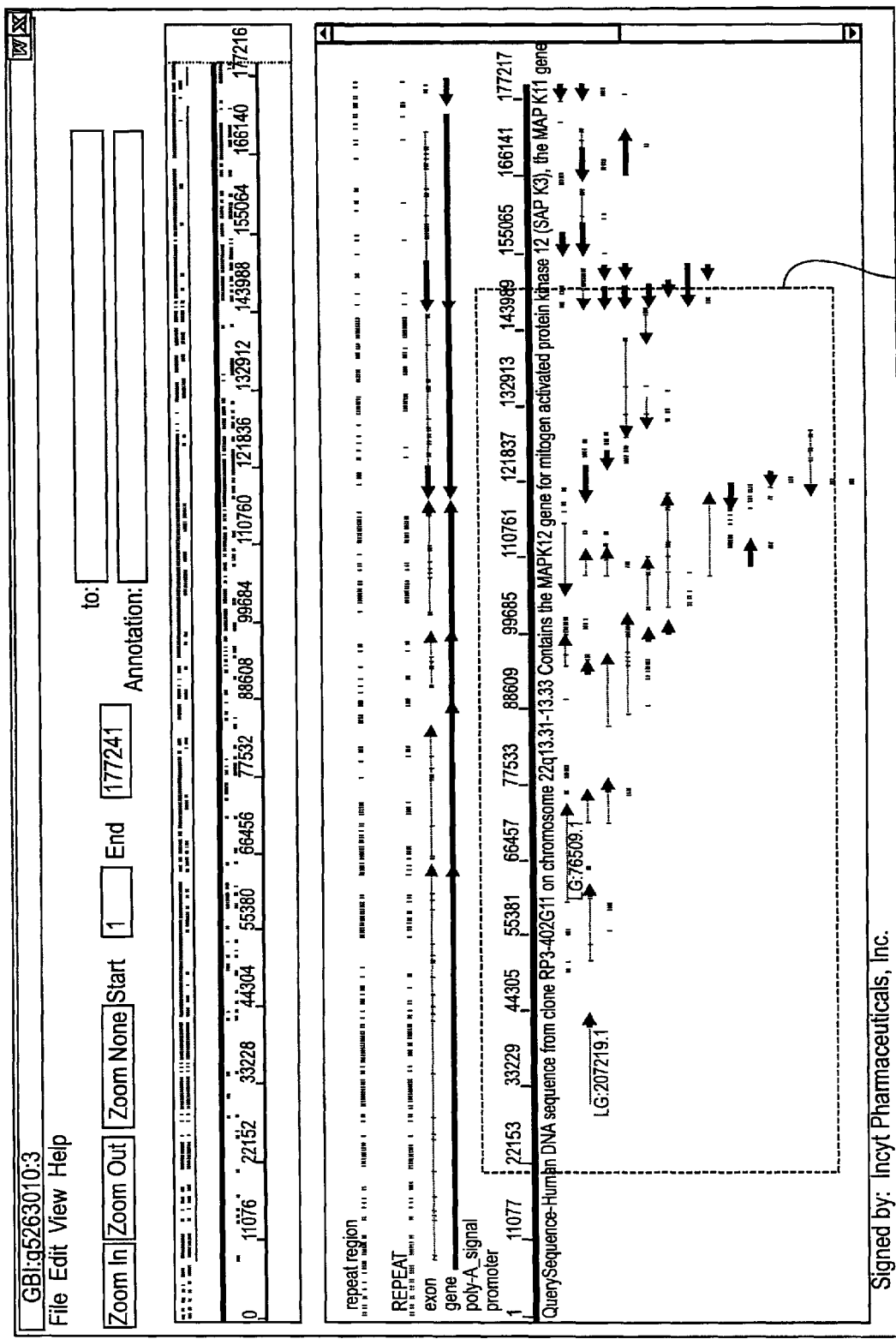
FIG. 5 is a screen shot as in FIG. 3 with a box around selected features in accordance with one embodiment of the present invention.
Figure 6:
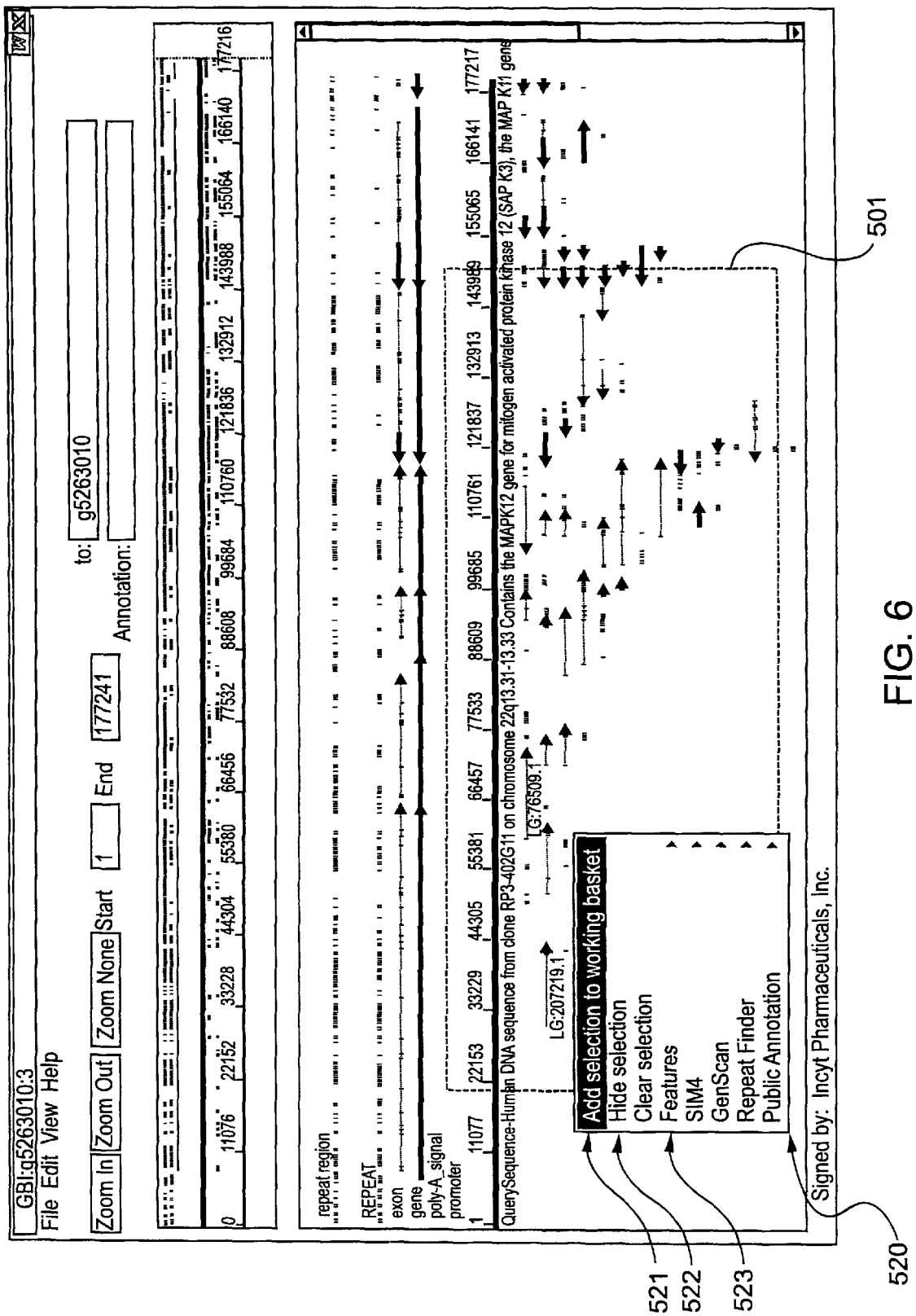
FIG. 6 is a screen shot depicting a main page of a biomolecular sequence graphical viewer showing a pull-down menu in accordance with one embodiment of the present invention.

One aspect contemplated by the inventors in a preferred embodiment of the present invention includes a Working Basket. The Working Basket is a way in which certain biomolecular sequences (in particular, features) can be selected from the viewer and subjected to further, more detailed analysis. With reference to FIG. 5, selected biomolecular sequences are enclosed by a colored box 501. (shown here with the dotted line). The biomolecular sequence contained within the box 501 can be selected as a group for addition to the Working Basket. Alternatively or additionally, individual features may be selected one by one for addition to the Working Basket. A preferred process for accomplishing this is depicted in FIG. 6. A red box 501 is placed around the desired biomolecular sequences. A pull-down menu 520 is activated. An "Add selection to working basket" button 521 is then activated which will add the selection to the Working Basket. The selection can be the plurality of biomolecular sequences (features) enclosed within the box 501 or can be individually selected features. Alternate methods of adding features to the Working Basket will be discussed below.

Referring again to FIG. 5, the features within the box 501 can be selectively manipulated to accomplish a variety of results. For example, the features enclosed by the box 501 may be selectively hidden. For example, referring again to FIG. 6, the hide selection button 522 of the pull-down menu 520 may be selected. As a result, all features within the box 501 are hidden from view, leaving viewable the remaining biomolecular sequence data lying outside the box. The hidden features may be stored in a Hidden Features basket (not shown) for ease of use. The remaining sequence data may be subjected to further detailed analysis, if desired. Additionally, the hiding can be even more selective. The features contained within the box 501 can be selectively "edited" by, for example, excluding all features which are obtained using, for example, specified methods. Also, specific types of features can be selectively hidden.

Figure 7:
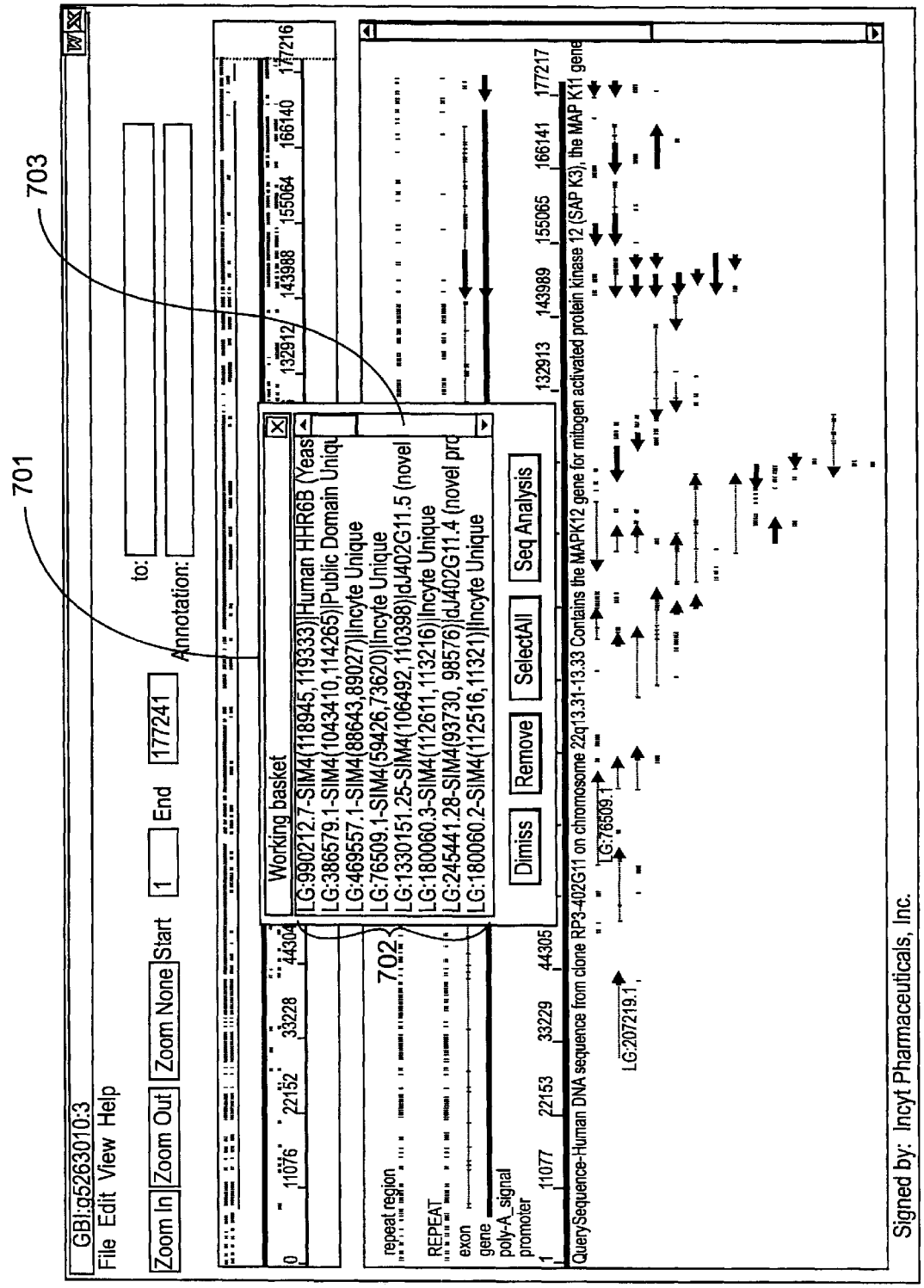
FIG. 7 is a screen shot depicting a working basket panel in accordance with an embodiment of the present invention.

Once the features are selected, they are added to the Working Basket. With reference to FIG. 7, the Working Basket 701 includes a plurality of sequences 702 which have been added to the Working Basket. The Working Basket 701 can contain a broad range of information including, but not limited to, feature LocusID, gene (functional) category, base pair range, database from which the biomolecular sequence data was retrieved (e.g., Incyte Life Seq Gold® database), the sequence's homologous matches (preferably the number of homologous matches returned is limited to a preset number; for example, one match) against other sequence databases, for example, the Genpept database, and other information useful to researchers and relating to other features of the database system with which the graphical viewer is used. Many of the fields of information provided in the window 701 may be hyperlinks to other HTML pages or other screens. A scroll bar 703 permits the features to be analyzed by scrolling up and down the Working Basket 701 to observe the features (sequences) of interest.

Figure 8:
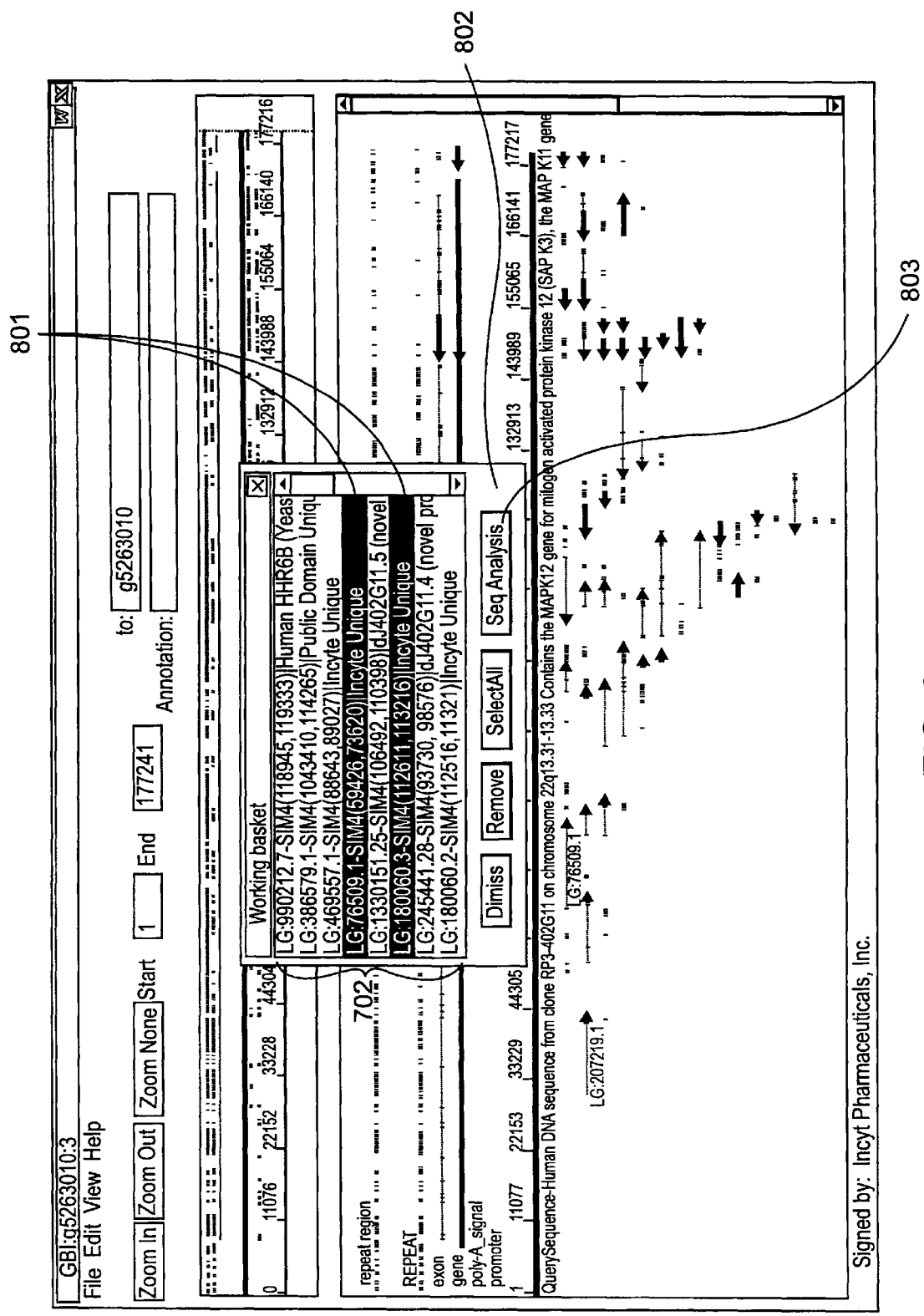
FIG. 8 is a depiction as in FIG. 7 with selected sequences highlighted for further detailed analysis in accordance with one embodiment of the present invention.
Figure 9:
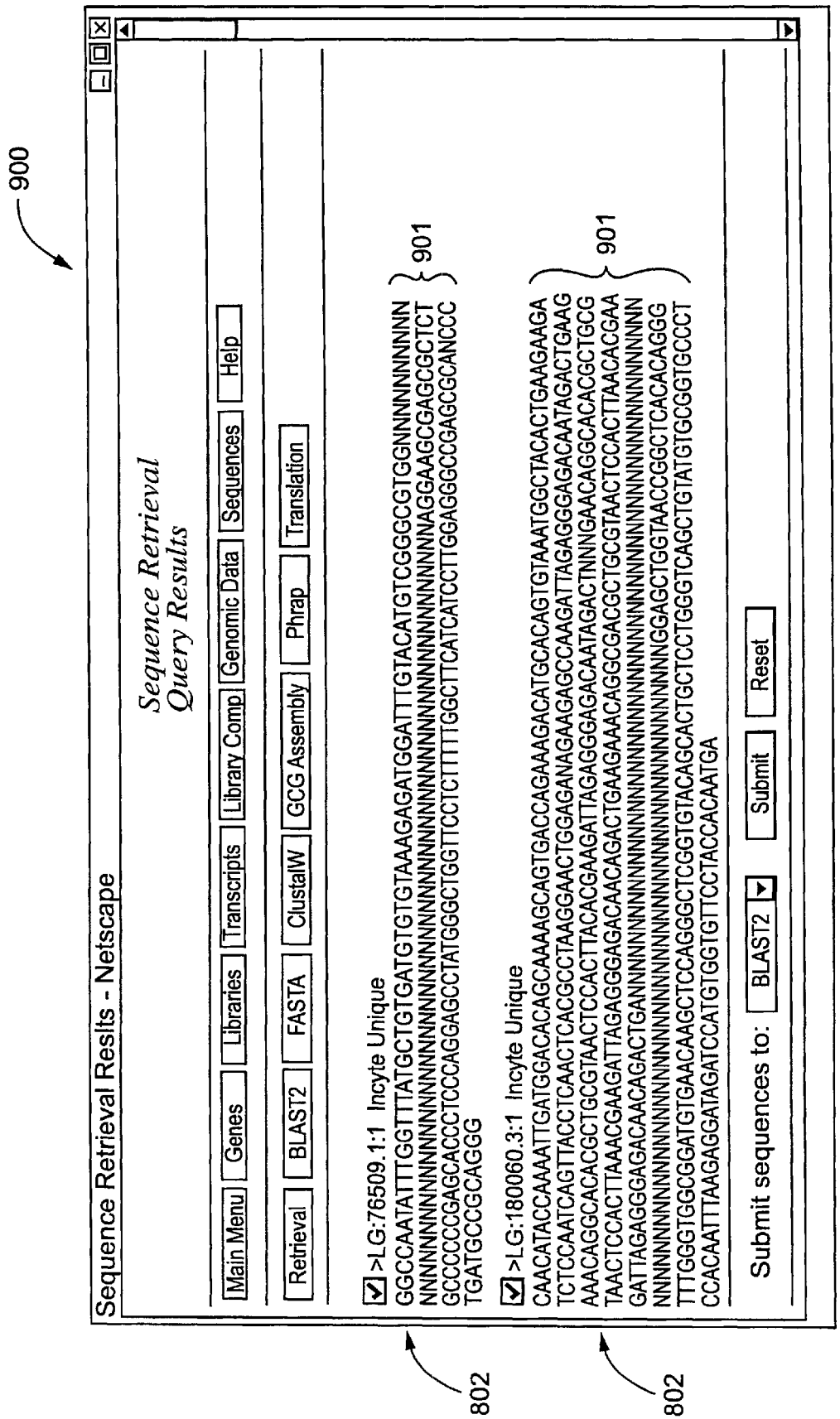
FIG. 9 is a depiction of DNA base pair sequences in accordance with an aspect of the present invention.

With reference to FIG. 8, selected features 801 are chosen from among the sequences 702 for further analysis. For example, the two selected sequences (LG:76509.1 and 180060.3) 801 are selected for further analysis using another analysis tool, for example, a scalable data source search engine which can store biomolecular sequence data (e.g., nucleotide and protein sequences). One example of such an engine is the SeqServer® database developed by Incyte Genomics, Inc. A row of buttons 802 allows access to further analysis. For example, referring to the line of buttons 802 a sequence analysis may be performed using the sequence analysis button 803. This button 803 will pass the selected features on to a sequence analysis tool, such as the SeqServer® database provided by Incyte Genomics, Inc. This sequence analysis tool provides a method of manipulating the features such that they may be analyzed in greater detail. With reference to FIG. 9, a sequence retrieval window 900 depicts the sequences of the two selected features 802. The sequences are identified using their locus ID's (76509.1 and 180060.3) and the database (in this case, "Incyte Unique", an internal database) from which they are drawn is identified. The sequences are shown as a series of base pairs 901. These sequences can also be submitted to further analysis tools using, for example, a BLAST 2 analysis.

Figure 10:
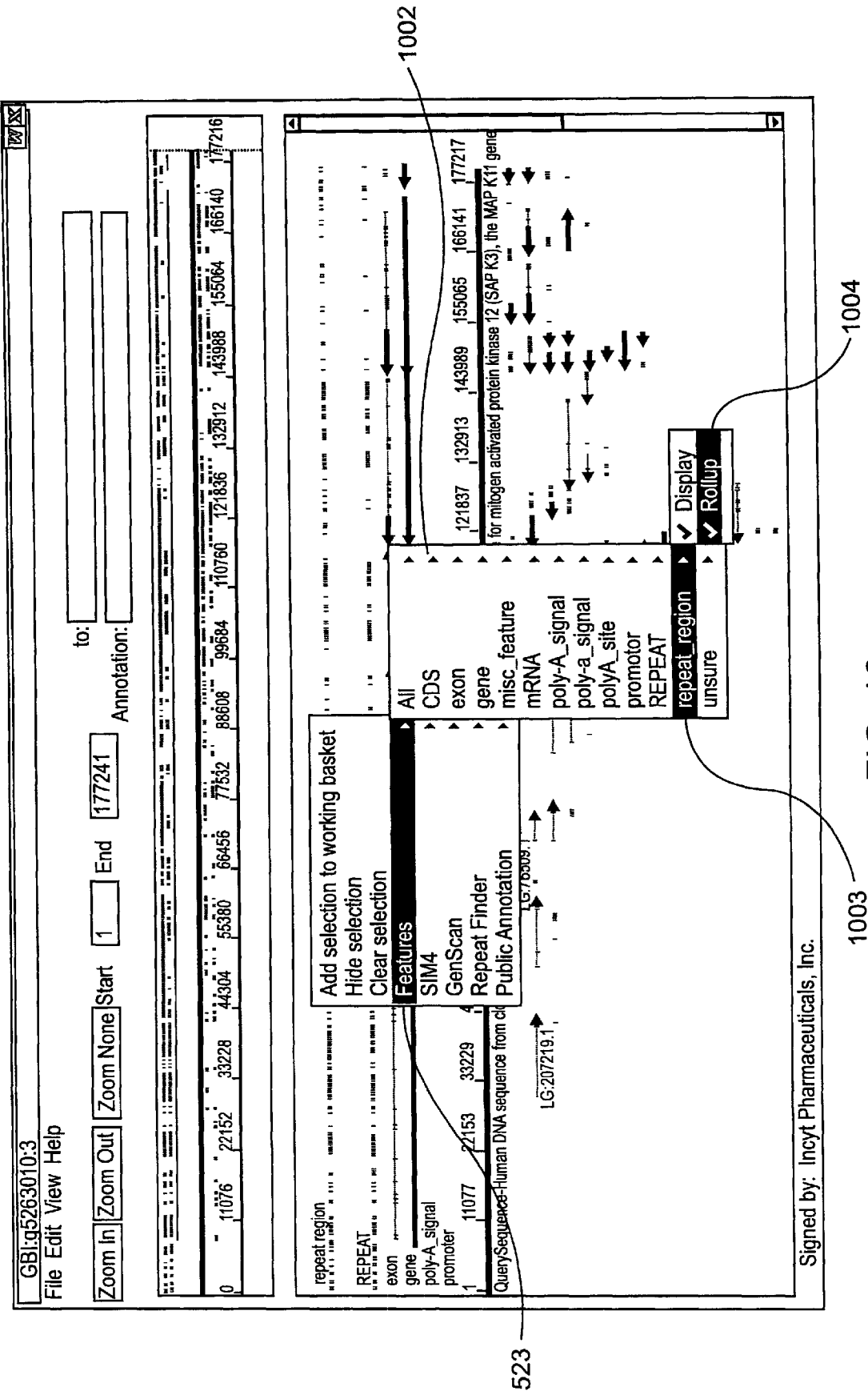
FIGS. 10 and 11 are screen shots depicting the operation of drop-down menus selecting the roll-up feature for examining sequencing information in accordance with one embodiment of the present invention.
Figure 11:
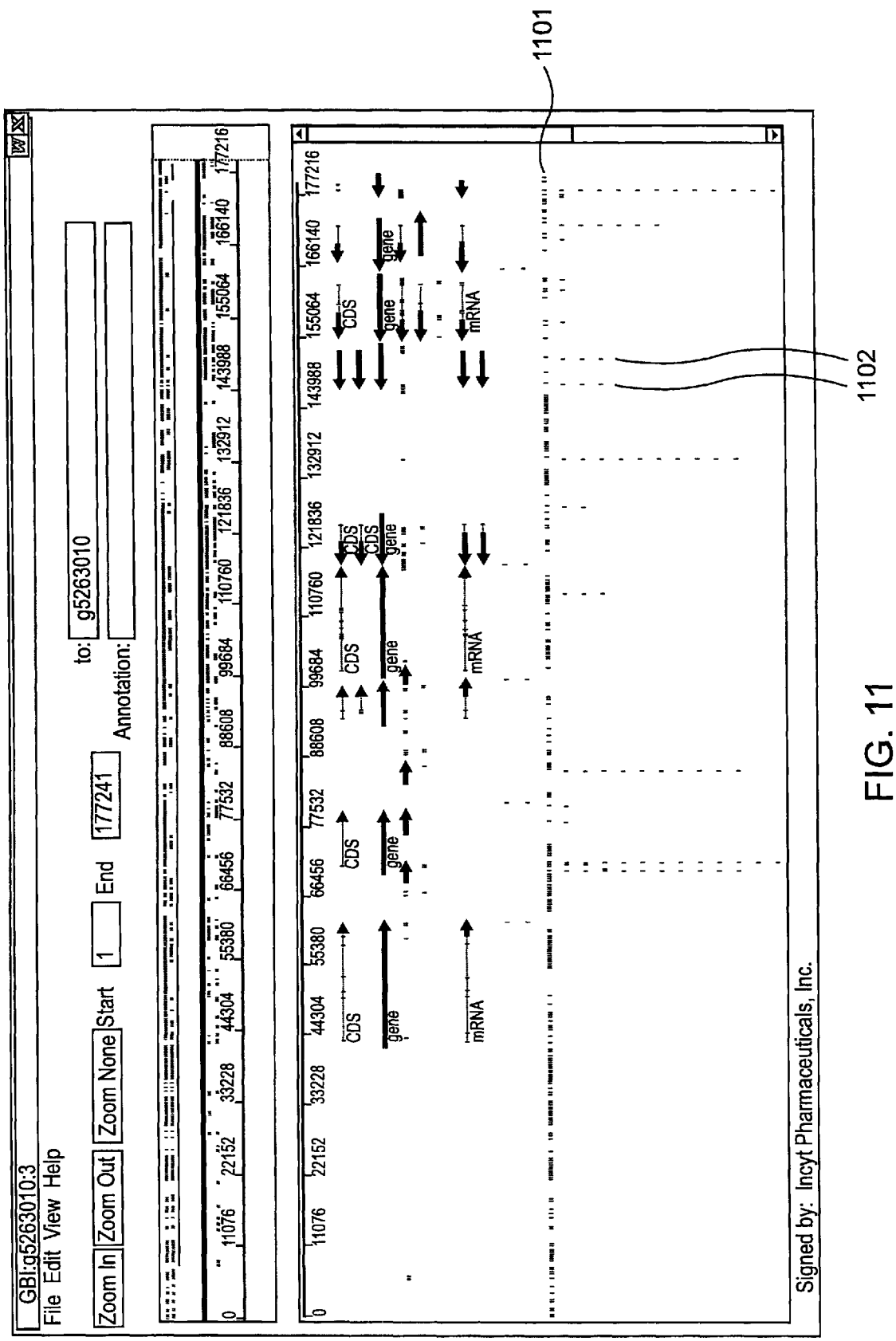

Referring again to FIG. 6, further detailed analysis of the biomolecular sequence data can be accomplished by selecting the "Features" button 523 of the pull down menu 520. Referring now to FIG. 10, the nature of coverage for each hit or feature can be ascertained. By selecting the "Features" button 523 another pull down menu 1002 is activated. By selecting the "repeat_region" button 1003 a "Rollup" button 1004 can be activated. As a result more detailed information concerning the precise number of hits that match a selected sequence becomes available. For example, as shown in FIG. 11 each feature has various portions of its biomolecular sequence sequenced. Various tools (also referred to herein as methods) are used to accomplish the sequence analysis of the biomolecular information contained within each feature or hit. For example, a BLAST analysis of a piece of biomolecular sequence data may yield many hits. This is reflected in the panel of FIG. 11. Hits which, for example, have only one BLAST match are depicted by the marks 1101. If a region has only one corresponding BLAST hit, no additional marks will appear below mark 1101. However, if the region has a number of corresponding hits, these hits may be examined by rolling down the panel along the y-axis. This can easily be seen, for example, with reference to the sequence depth indicators 1102. These indicators 1102 show that the selected region has many hits, for example, four hits. Each little tick mark can, for example, represent one hit. Alternatively, the tick marks can represent more than one hit. This is especially appropriate where sequence data has many hits. Thus, this tool provides a user with a way of quickly discerning the number of hits over each queried sequence. Additionally, the ticks can be in different colors. Each color representing a different method or analysis tool used to obtain the hit information (e.g., using a BLAST analysis). Thus, not only can the number of hits be discerned but the methods by which the hit information was obtained can also be readily discerned upon cursory examination.

The manner in which this hit and feature information is depicted provides a further illustration of the power of a graphical viewer in accordance with the present invention in presenting information in a highly effective manner. A user of the graphical viewer is able to very quickly, at a glance, assimilate useful information relating to the sequence information depicted in the other panels of the viewer. In this preferred embodiment of the present invention, the hit or feature information can be displayed, for example, in the bottom portion of the target viewer 430. A particular advantage of depicting the coverage information in this way is that it is particularly effective for clearly providing this information in a graphical format which makes a clear visual impression and renders the data easily quantifiable, with reference to, for example, a y-axis scale (not shown). The hit data for various regions is also easily compared in this format.

In other embodiments of the invention, a sequence depth may graphically depict the depth of coverage information in other ways. For example, the actual sequences from which the sequence was assembled may be depicted. This way of depicting the sequence coverage information may provide useful information for some users who are concerned with the data acquisition process, for example, used in the sequence's formation.

Also, graphical viewer embodiments, in accordance with the principle of the present invention, include a menu bar (See, FIG. 3, 404) for accessing pull-down menus listing various command and control functions. A File pull-down menu lists standard commands found in applications software packages such as save, close, and print, etc. An Edit pull-down menu provides a list of categories for editing the parameters of the graphical viewers, including the colors used to represent various features in the viewers.

Figure 12:
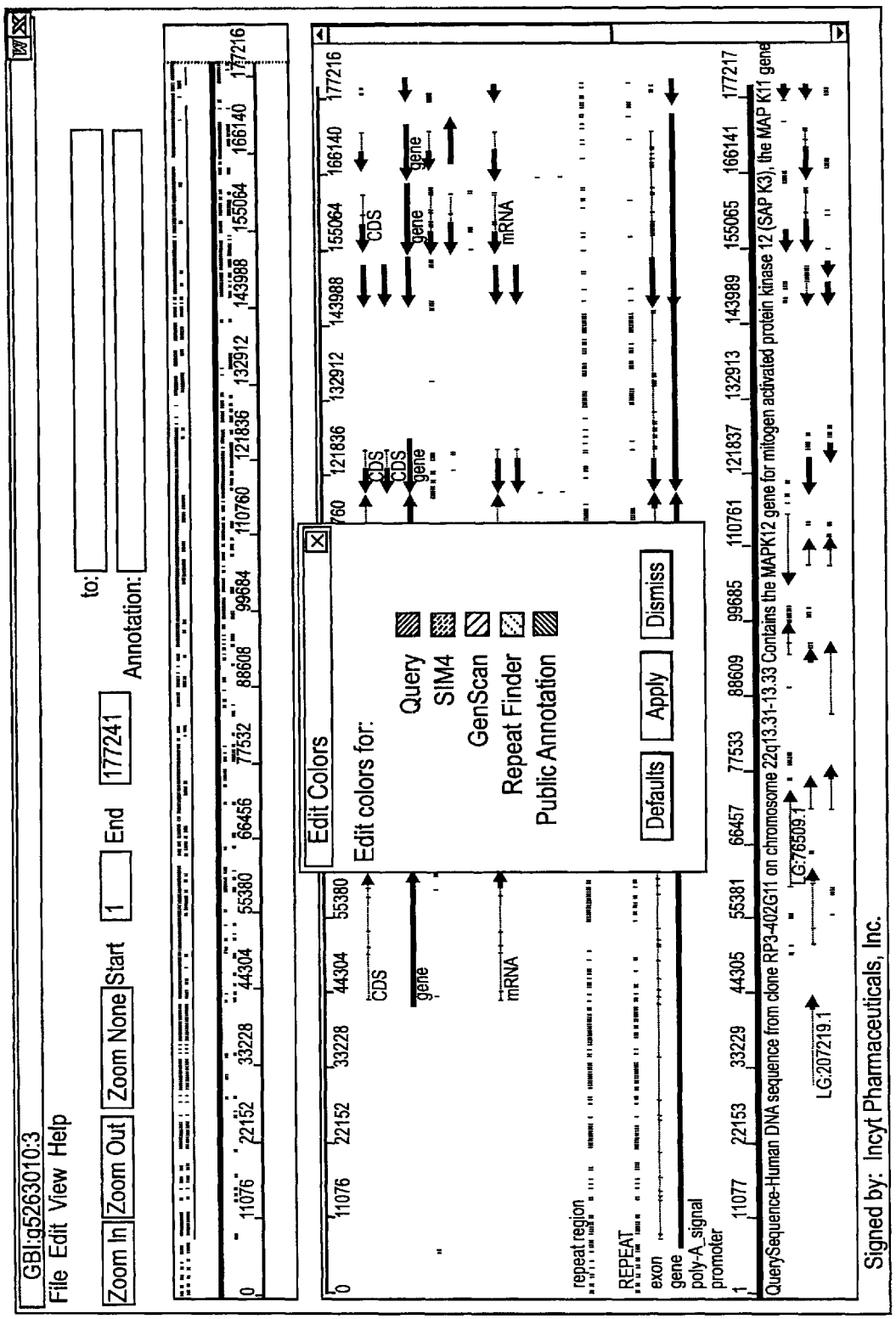
FIG. 12 is a drop-down menu used for editing colors used for annotations, methods, repeat finders, and queries in a view embodiment in accordance with the present invention.
Figure 13:
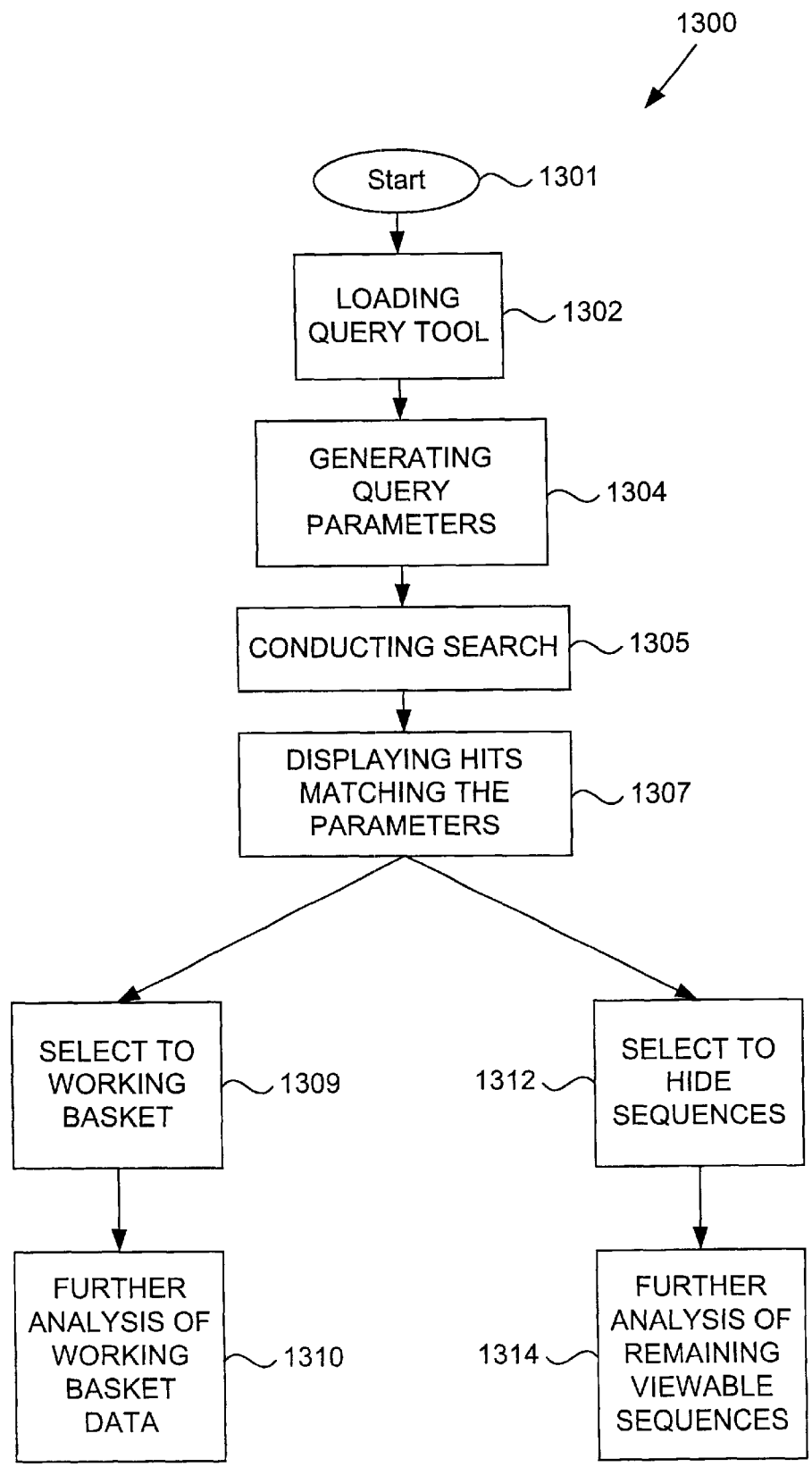
FIG. 13 is a flow chart depicting a process flow by which biomolecular sequence information may be viewed and analyzed with a biomolecular sequence graphical viewer in accordance with a preferred embodiment of the present invention.

Furthermore, the aspect of changing the colors used for each analysis tool is further elaborated upon in FIG. 12. Each color reflects a different analysis tool used to define the sequence information. As shown in FIG. 12, these tools may include, but are not limited to, query tools, tools that align CDNA to genomic sequences (e.g., SIM 4), gene prediction tools (e.g., Gen Scan), Repeat Finder, or Public Annotation. Each of the tools being assigned a color by default or using user assigned colors.

A generalized process 1300 of one method embodiment in accordance with the present invention begins at 1301 and ends at a step 1302 for selecting and loading an appropriate query tool. The tools available are numerous, and may include query tools produced by Incyte Genomics, Inc., such as LifeSeq® Gold. Once the query tool is properly loaded, a sequence search is effected. This begins by generating query parameters 1304. Examples of these parameters include database sources which can be individually selected or group selected. The databases may, as explained previously, be selected from among proprietary databases or public databases. Further useful parameters are molecule type, e.g., protein or nucleotide or both. Additionally, a keyword may be input to more accurately locate the desired sequence. This keyword may be a precise sequence nomenclature (a sequence ID or locus ID) or other more general term used to locate a biomolecular sequence. For example, "kinase" may be used as a keyword. Additionally, a sequence ID number may be used to search the desired biomolecular sequence data. A search is conducted using the chosen query tools 1305. Once the search is finished, the query results may be displayed 1307. The biomolecular sequence data which matches the query parameters may be displayed. This data may be selected from a list in an HTML page provided as part of a user interface of a biomolecular sequence relational database in connection with which the present graphical viewer is used. The data is displayed, preferably using a graphical display having a plurality of components for representing and showing detailed information about the query hits matching the query parameters.

Another feature of this aspect of a preferred embodiment of the present invention is a Working Basket, as described above. A user may elect to display a Working Basket viewer into which elements of the displayed biomolecular sequence data may be stored and displayed 1309. The Working Basket information may optionally be subjected to further analysis 1310. Such analysis may include sequence depth analysis, examination of specific sequences contained in the Working Basket.

Alternatively, selected sequences may be hidden from view on the viewers. These sequences will be selected either individually or as groups. Also, these sequences may be selected by methods used to determine the sequence information. Still further, the sequences may be hidden by feature type. For example, hide all proteins. Features useable for this purpose include, but are not limited to, proteins, DNA, RNA, exons, introns, CDS, STS, gene sequences, mRNA, snRNA, poly-A sites, poly-A signals, promoters and the like. The remaining viewable sequences can then be subject to further analysis, if desired.

As with other data displayed in graphical viewers in accordance with the present invention, the data used in this aspect of the invention is obtained from an associated biomolecular sequence database and system. The organization and operation of such systems may vary. Examples are provided in the Incyte Genomics applications previously incorporated by reference herein. Given the description of the functionality and displays herein, one of skill in the art would be able to implement the graphical viewer of the present invention in any such system.

Data Format

One advantage of an embodiment in accord with the principles of the present invention is that a graphical viewer embodiment is capable of receiving and depicting data accessed from a variety of different data sources. Further, the data from the different data sources need not have the same format in order to function in conjunction with the viewer of the present invention, as long as the data sources accessed by the viewer have certain data fields. Such data may even be received in simple text format. Moreover, as long as the data includes at a minimum, a data field containing a start coordinate and a data field containing an end coordinate, it is readable by the graphical viewer embodiments of the present invention. However, more enhanced application embodiments are contemplated by the inventors, such embodiments can include an expanded range of data fields. Each object handler requires a certain set of data fields in order to operate properly. Moreover, the data fields needed for each object handler can be different. However, as long as the data received by the viewer from the data source includes the minimum number of data fields necessary to support the associated object handlers the viewer can display and use the data. Typical, useful fields include, for example, fields for features, hits, methods (that is, analysis tools), query object, and unique features. In one preferred embodiment, as long as the data contained in an accessed data source includes data objects preceded by a Java®-class handler defining the characteristics of the data object field, for example chosen from among a Query Object handler, a Hit Object handler, a Method Object handler, and a Unique Features handle, the data will be compatible with the viewer of the present embodiment. Alternatively, if the data source has an Object handler which enables it to convert the data from the existing data source format to a data format which includes data objects preceded by a Java®-class handler chosen from, among, for example a Query Object handler, a Hit Object handler, a Method Object handler, and a Unique Features handler, such data will also be accessible by this embodiment of the present invention. An example of a typical Query Object handler follows: (Please note that the "|" symbol is used as a column separator. All columns must be present even if not used.)

COM.Incyte.product11.igp.data.IGPQueryObjectHandler

QuerySequence|Human DNA sequence from 4PTEL, Huntington's Disease Region, chromosome 4p16.3.|1|118767

Wherein the columns are as follows:

Column 1: Name of query sequence as shown on viewer
Column 2: Description of sequence
Column 3: Start coord
Column 4: End coord A typical Object handler is described by the following:

COM.Incyte.product11.igp.data.IGPHitObjectHandler
35781|28901|GP|g437444|1|DNA-binding protein|BLASTX|+|Protein
max_blast_e_value|4e-05|0.000040
min_blast_e_value|1e-125|0.000000
END_METRICS
49293|49451|1|53
49452|49460|58|60
75717|75782|204|225
75798|75803|226|227
75804|75941|230|275
75813|75950|289|334
75813|75962|345|394
END Line 1:
Column 1: HitAnnotationID
Column 2: MimeID
Column 3: Target SeqSource
Column 4: Target SeqID
Column 5: Target SeqVersion
Column 6: Description
Column 7: MethodName
Column 8: Direction (+/−)
Column 9: Type (Protein/Nucleotide)

Line 2 up until END_METRICS
Column 1: name of sort metric
Column 2: metric to display
Column 3: metric to use when sorting
Note: If no metrics are available END_METRICS must still show up on a separate line Line 5 up until END
Column 1: Query start coord
Column 2: Query end coord
Column 3: Target start coord
Column 4: Target end coord
Note: END must appear to indicate the end of this hit object An exemplar Feature Object handler includes the following:

COM.Incyte.product11.igp.data.IGPFeatureObject Handler
GBI|g2121307|1REPEAT|L1,MIR,MaLR-LTR|243|Repeat Finder|0|+15387|15423|N|A
END
END_METRICS Line 1:
Column 1: SeqSource
Column 2: SeqID
Column 3: SeqVersion
Column 4: FeatureKey
Column 5: Feature Description
Column 6: FeatureOccurrence
Column 7: Method Name
Column 8: MimeID
Column 9: Direction (+/−)

Line 2 up until END
Column 1: Segment start
Column 2: Segment end
Column 3: Segment description Line 4 up until END_METRICS
Column 1: name of sort metric
Column 2: metric to display
Column 3: metric to use when sorting
Note: If no metrics are available END_METRICS must still show up on a separate line A typical Unique Features handler includes:
COM.Incyte.product11.igp.data.IGPUniqueFeatures Handler
UniqueFeatures
REPEAT
exon
gene
poly-A_signal
promotor
repeat_region
END
Line 1 name of object
Line 2 up until END: each unique feature key from the list of feature objects returned to the viewer Invention Implementation It is important to note that the present invention may be implemented as a system or a method, and may be embodied on a variety of computer-readable media that include program instructions, etc. for performing various operations described herein. As noted above, the system implementation is preferably in association with a biomolecular sequence relational database system. The method is a computer-implemented method, generally involving the operation of such a system. The media may be any computer-readable media. Examples of computer-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention may also be embodied in a carrier wave travelling over an appropriate medium such as airwaves, optical lines, electric lines, etc.

Conclusion

Although the foregoing invention has been described in some detail for purposes of clarity of understanding, it will be apparent that certain changes and modifications may be practiced within the scope of the appended claims. It should be noted that there are many alternative ways of implementing methods, media and systems of the present invention. As noted previously, the scope of the invention is not limited to use with a human genomic database system such as that in connection with which the invention is primarily described above. Given the description provided herein, one of skill in the art would understand how to use the present invention in connection with a variety of computer-based biomolecular sequence database systems. For example, a graphical viewer in accordance with the present invention may be used in connection with database systems employed to store and analyze other types and forms of nucleic acid sequences or expressed nucleic acid or amino acid sequences. Accordingly, the present embodiments are to be considered as illustrative and not restrictive, and the invention is not to be limited to the details given herein, but may be modified within the scope and equivalents of the appended claims.

We claim:

1. A computer-readable medium having programming instructions arranged to graphically display biomolecular sequence data, the programming instructions including programming instructions for:

retrieving biomolecular sequence data from a database containing biomolecular sequence data;

graphically depicting elements of the biomolecular sequence data in a user interface of a computer system, graphically selecting one or more components of the biomolecular sequence data as a group.

2. In a computer-readable medium as in claim 1, wherein the programming instructions include programming instructions for retrieving biomolecular sequence data from a database in response to a user query, selectably graphically depicting information indicating the number and type of sequencing operations used to determine the one or more components of the biomolecular sequence data.

3. In a computer-readable medium, as in claim 2, wherein the programming instructions for graphically depicting the retrieved biomolecular sequence data include instructions for displaying the retrieved biomolecular sequence data in plurality of panels occupying a single frame of the user interface.

4. In a computer-readable medium, as in claim 2, wherein the programming instructions further include instructions for further analysis of the graphically selected one or more components of biomolecular sequence data.

5. In a computer-readable medium, as in claim 4, wherein the programming instructions further include instructions for depicting the graphically selected one or more components of biomolecular sequence data in a working basket panel.

6. In a computer-readable medium, as in claim 5, wherein the programming instructions further include instructions for conducting a more detailed analysis of the graphically selected one or more components of biomolecular sequence data in the working basket accomplished by instructions for manipulating the sequence data in the working basket.

7. In a computer-readable medium, as in claim 6, wherein the programming instructions for conducting detailed analysis of the graphically selected one or more components of biomolecular sequence data in the working basket include instructions for examining the specific base pairs of the biomolecular sequences in the working basket.

8. In a computer-readable medium, as in claim 6, wherein the programming instructions for conducting detailed analysis of the graphically selected one or more components of biomolecular sequence data in the working basket include instructions for examining the specific polypeptide sequence of the biomolecular sequences in the working basket.

9. In a computer-readable medium, as in claim 6, wherein the programming instructions for conducting detailed analysis of the graphically selected one or more components of biomolecular sequence data in the working basket include instructions for manipulating the graphically selected one or more components of biomolecular sequence data in the working basket using other data analysis tools.

10. In a computer-readable medium, as in claim 2, wherein the programming instructions further include instructions for hiding from view the graphically selected one or more components of biomolecular sequence data leaving viewable remaining biomolecular sequence data.

11. In a computer-readable medium, as in claim 10, wherein the programming instructions for hiding from view the graphically selected one or more components of biomolecular sequence data further includes programming instructions for selecting one or more components of the viewable remaining biomolecular sequence data by feature type.

12. In a computer-readable medium, as in claim 10, wherein the programming instructions for hiding from view the graphically selected one or more components of biomolecular sequence data further includes programming instructions for selecting one or more components of the viewable remaining biomolecular sequence data by analysis tool type.

13. In a computer-readable medium, as in claim 10, wherein the programming instructions further include instructions for analyzing the viewable remaining biomolecular sequence data, wherein the number and type of sequencing operations used to generate the viewable remaining biomolecular sequence data can be further analyzed by scrolling up and down the panels.

14. A computer-implemented method for presenting biomolecular sequence data, comprising:

retrieving biomolecular sequence data from a database in response to a user query;

graphically depicting elements of the biomolecular sequence data in a user interface for said computer system, wherein graphically depicting elements of the biomolecular sequence data includes depicting the elements of the biomolecular sequence data in a plurality of panels; and graphically selecting of one or more components of the biomolecular sequence data.

15. A method as in claim 14 wherein, the plurality of panels are comprised within a single frame.

16. A method as in claim 15 wherein, the plurality of panels graphically depict different aspects of the biomolecular sequence data.

17. A method as in claim 16 wherein the different aspects of the biomolecular sequence data include biomolecular sequence hits responsive to the user query and features which are biomolecular sub-sequences which are portions of the hits.

18. A method as in claim 17 wherein the features include biomolecular sub-sequences selected from the group of sub-sequences consisting of DNA sequences, RNA sequences, protein sequences, CDS sequences, STS sequences, exons, gene sequences, mRNA sequences, polyA sites, polyA signals, promoters, and snRNA sequences.

19. The method of claim 14, wherein the plurality of panels include a first legend panel graphically depicting at least a portion of a sequence associated with a reference ID, and a second target panel graphically depicting at least a portion of the sequence depicted in said legend panel and a third panel for graphically depicting additional sequence information.

20. A method as in claim 14 wherein said graphically selecting of one or more components of the biomolecular sequence data is accomplished by using one of: graphically selecting the one or more components of the biomolecular sequence data in groups of biomolecular sequence data or individually selecting the biomolecular sequence data.

21. A method as in claim 20 wherein said graphically selecting of the one or more components of the biomolecular sequence data can be further enhanced by selected the one or more components of the biomolecular sequence data by feature type.

22. A method as in claim 20 wherein said graphically selecting of the one or more components of the biomolecular sequence data can be further enhanced by selected the one or more components of the biomolecular sequence data by analysis tool used to analyze the one or more components of biomolecular sequence data.

23. A method as in claim 20 further including storing the graphically selected one or more components of the biomolecular sequence data in a working basket.

24. A method as in claim 23 wherein said graphically selected one or more components of biomolecular sequence data in the working basket are subjected to detailed analysis accomplished by manipulating the sequence data in the working basket.

25. The method of claim 23, further including displaying the graphically selected one or more components of the biomolecular sequence data stored in the working basket in a working basket panel and wherein the method further includes analyzing the graphically selected one or more components of the biomolecular sequence data displayed in the working basket panel.

26. The method of claim 25, wherein said analyzing of the biomolecular sequence data displayed in the working basket panel comprises selectably indicating the number and type of sequencing operations used to determine the biomolecular sequence data in the working basket panel.

27. The method of claim 25, wherein said analyzing of the biomolecular sequence data displayed in the working basket panel comprises selectably indicating the specific base pair sequence of the biomolecular sequence data in the working basket panel.

28. The method of claim 20, wherein said graphically selecting of one or more components of the biomolecular sequence data is analyzed by scrolling up and down the selected one or more components of the biomolecular sequence data to view a more detailed version of the number and type of sequencing operations used to determine the biomolecular sequence data.

29. The method of claim 28, wherein said more detailed version of the number and type of sequencing operations used to determine the biomolecular sequence data is viewable along the y-axis by scrolling up and down the selected one or more components of the biomolecular sequence.

30. A method as in claim 19 further including storing the graphically selected one or more components of the biomolecular sequence data in a working basket.

31. The method of claim 19, further including displaying the graphically selected one or more components of the biomolecular sequence data stored in the working basket in a working basket panel and wherein the method further includes analyzing the graphically selected one or more components of the biomolecular sequence data displayed in the working basket panel.

32. The method of claim 31, wherein the analyzing of the graphically selected one or more components of the biomolecular sequence data displayed in the working basket panel comprises selectably indicating the number and type of sequencing operations used to determine the biomolecular sequence data in the second reference panel.

33. The method of claim 32, wherein said analyzing of the graphically selected one or more components of the biomolecular sequence data displayed in the working basket panel is achieved by scrolling up and down the working basket panel to view a more detailed version of the biomolecular sequence data pertaining to the number and type of sequencing operations used to determine the biomolecular sequence data in the second reference panel.

34. The method of claim 19, further includes analyzing, in detail, the third panel wherein the number and type of sequencing operations are viewed by scrolling up and down the sequence depth panel.

35. The method of claim 20, further including highlighting the graphically selected one or more components of the biomolecular sequence data.

36. The method of claim 35, wherein the graphically selected biomolecular sequence data are hidden from view on one or more of the plurality of panels leaving viewable certain remaining biomolecular sequence data.

37. The method of claim 36, further includes analyzing, in detail, said viewable remaining biomolecular sequence data, wherein each component of said viewable biomolecular sequence data is analyzed by scrolling up and down panels wherein the viewable biomolecular sequence data is displayed.

38. The method of claim 37, wherein said analyzing of each component of said viewable biomolecular sequence data by scrolling up and down the panels includes analyzing the number and type of sequencing operations used to generate biomolecular sequence data.

39. The method of claim 14, further being implemented using the JAVA programming language.

40. A computer system, comprising:
a data source including biomolecular sequence data configured in a format having a plurality of data fields including data objects independent of the source of the data;
a user interface capable of:
receiving from the data source, biomolecular sequence data responsive to a query,
graphically displaying the received biomolecular sequence data in a plurality of panels; and
wherein the data source is configured such that each data object is preceded by an object handler which defines the data object field.

41. The computer system of claim 40 wherein the data object fields comprise a query field, a hit field, a feature field, a method field, and a unique feature field.

42. The computer system of claim 40 wherein the object handlers include a query object handler, a hit object handler, a feature object handler, and a method object handler, a unique features object handler.

43. The computer system of claim 40 wherein the database is configured to include an object handler which can reformat the biomolecular sequence data into a plurality of data fields which include a query object handler, a hit object handler, a feature object handler, a method object handler, and a unique features object handler.

44. The computer system of claim 42 wherein the user interface is further capable of initiating a user query relating to the biomolecular sequence data.

45. The computer system of claim 44 wherein the user interface graphically depicts different aspects of the selected biomolecular sequence data in the plurality of panels.

46. A method as in claim 45 wherein the different aspects of the biomolecular sequence data include biomolecular sequence hits responsive to the user query and features which are biomolecular sub-sequences which are portions of the hits.

47. A method as in claim 46 wherein the features include biomolecular sub-sequences selected from the group of sub-sequences consisting of DNA sequences, RNA sequences, protein sequences, CDS sequences, STS sequences, exons, gene sequences, mRNA sequences, polyA sites, polyA signals, promoters, and snRNA sequences.

48. A method as in claim 45 wherein the different aspects of the biomolecular sequence data gene locus data.

49. The computer system of claim 46, wherein the plurality of panels include a first legend panel graphically depicting at least a portion of a sequence associated with a reference ID, a second reference panel graphically depicting at least a portion of the sequence depicted in said legend panel, and a third panel indicating the number and type of sequencing operations conducted to determine the sequence data depicted in the sequence depth panel.

50. The computer system of claim 49, wherein the number and type of sequencing operations graphically depicted in the third panel can be analyzed, in detail, by scrolling up and down the third panel to view the number and type of sequencing operations used to generate the depicted biomolecular sequence data.

51. The computer system of claim 46 wherein the user interface for selecting the desired features and hits accomplishes the selecting using one of: selecting the desired features and hits in a group or individually selecting the desired features and hits.

52. The computer system of claim 51 wherein the said selected desired features and hits are hidden from display on the user interface and analysis can be performed on the features and hits displayed on the user interface.

53. The computer system of claim 51 wherein the selected desired features and hits are stored in a working basket for further analysis.

54. A computer system, comprising:
a data source including biomolecular sequence data configured in a format having a plurality of data fields including data objects independent of the source of the data;
a user interface capable of:
receiving from the data source, biomolecular sequence data responsive to a query,
graphically displaying the received biomolecular sequence data in a plurality of panels; and
wherein the data source is configured such that each data object includes a start coordinate data field and an end coordinate data field.

55. The computer system of claim 54 wherein each data object includes additional data fields which satisfy the requirements of object handlers used to receive biomolecular sequence data from the data source and graphically display the received biomolecular sequence data in the plurality of panels.

56. The computer system of claim 55 wherein the additional data fields include a query field, a hit field, a feature field, a method field, and a unique feature field.

57. The computer system of claim 55 wherein the object handlers include a query object handler, a hit object handler, a feature object handler, and a method object handler, a unique features object handler.

58. The computer system of claim 54 wherein the data source is configured to include an object handler which can reformat the biomolecular sequence data into a plurality of data fields which include a query object handler, a hit object handler, a feature object handler, a method object handler, and a unique features object handler.

59. The computer system of claim 55 wherein the user interface is further capable of initiating a user query relating to the biomolecular sequence data.

60. The computer system of claim 55 wherein the user interface graphically depicts different aspects of the selected biomolecular sequence data in the plurality of panels.

61. A method as in claim 60 wherein the different aspects of the biomolecular sequence data include biomolecular sequence hits responsive to the user query and features which are biomolecular sub-sequences which are portions of the hits.

62. A method as in claim 61 wherein the features include biomolecular sub-sequences selected from the group of sub-sequences consisting of DNA sequences, RNA sequences, protein sequences, CDS sequences, STS sequences, exons, gene sequences, mRNA sequences, polyA sites, polyA signals, promoters, and snRNA sequences.

63. A method as in claim 62 wherein the different aspects of the biomolecular sequence data gene locus data.

* * * * *

UNITED STATES PATENT AND TRADEMARK OFFICE
CERTIFICATE OF CORRECTION

PATENT NO. : 6,611,828 B1  Page 1 of 1
DATED : August 26, 2003
INVENTOR(S) : Koleszar et al.

It is certified that error appears in the above-identified patent and that said Letters Patent is hereby corrected as shown below:

Column 23,
Line 2, replace "handier" with -- handler --
Lines 7 and 11, replace "data souce" with -- database --

Signed and Sealed this

Twenty-fifth Day of May, 2004

JON W. DUDAS
*Acting Director of the United States Patent and Trademark Office*